United States Patent
Satoh et al.

(10) Patent No.: US 7,592,424 B2
(45) Date of Patent: Sep. 22, 2009

(54) ION CHANNEL-LIKE POLYPEPTIDE AND USE THEREOF

(75) Inventors: Noriyuki Satoh, Kyoto (JP); Yasushi Okamura, Okazaki (JP); Hirohide Iwasaki, Okazaki (JP); Yoshimichi Murata, Okazaki (JP)

(73) Assignees: Kyoto University, Kyoto (JP); National Institutes of Natural Sciences, Tokyo (JP)

( * ) Notice: Subject to any disclaimer, the term of this patent is extended or adjusted under 35 U.S.C. 154(b) by 40 days.

(21) Appl. No.: 11/667,756

(22) PCT Filed: May 13, 2005

(86) PCT No.: PCT/JP2005/008807

§ 371 (c)(1),
(2), (4) Date: May 15, 2007

(87) PCT Pub. No.: WO2006/054371

PCT Pub. Date: May 26, 2006

(65) Prior Publication Data

US 2008/0182315 A1 Jul. 31, 2008

(30) Foreign Application Priority Data

Nov. 16, 2004 (JP) .............................. 2004-332070

(51) Int. Cl.
*C07K 14/705* (2006.01)
*C07K 14/435* (2006.01)
*C07K 14/00* (2006.01)
*C07K 7/00* (2006.01)
*C07K 7/08* (2006.01)

(52) U.S. Cl. ..................... 530/350; 530/300; 530/327

(58) Field of Classification Search ...................... None
See application file for complete search history.

(56) References Cited

FOREIGN PATENT DOCUMENTS

| | | |
|---|---|---|
| JP | 2004-057129 | 2/2004 |
| JP | 2004-057127 | 2/2007 |

OTHER PUBLICATIONS

Spafford et al. (1998). A putative voltage-gated sodium channel alpha subunit (PpSCN1) from the hydrozoan jellyfish, *Polyorchis penicillatus*: structural comparisons and evolutionary considerations. Biochemical and Biophysical Research Communications. 244(3):772-780.*
Wells, J.A. (1990). Additivity of mutational effects in proteins. Biochemistry. 29(37):8509-8517.*
Ngo et al. (1994). Computational complexity, protein structure prediction, and the Levinthal paradox. In Merz and Le Grand (Eds.) The Protein Folding Problem and Tertiary Structure Prediction. Birkhauser:Boston, pp. 491-495.*
Skolnick et al. (2000). From genes to protein structure and function: novel applications of computational approaches in the genomic era. Trends in Biotechnology. 18:34-39.*
International Search Report (PCT/ISA/210), 2005.
Okamura, Yasushi et al. "Survey of Ion Channel Molecules from *Ciona* Genome". Jpn. J. Physiol., vol. 54, Suppl, p. S20, S46(S11-2), May 17, 2004.
Satou, Yutaka et al. "Gene Expression Profiles in *Ciona intestinalis* Tailbud Embryos". Development, vol. 128, pp. 2893-2904 (2001).
Thomas, L. et al. "Mapping of Residues Forming the Voltage Sensor of the Voltage-Dependent Anion-Selective Channel". Proc. Natl. Acad. Sci. USA, vol. 90, pp. 5446-5449 (1993).

* cited by examiner

*Primary Examiner*—Christine J Saoud
*Assistant Examiner*—Jon M Lockard
(74) *Attorney, Agent, or Firm*—Harness, Dickey & Pierce, P.L.C.

(57) ABSTRACT

A single polypeptide is disclosed that without the need of any direct ion flow, is capable of converting electrical signals to chemical signals. The polypeptide of at least one embodiment of the present invention can be a novel membrane protein including a specified domain capable of independently functioning as a potential sensor and another domain exhibiting a phosphatise activity. In one potential embodiment, the polypeptide preferably consists of the $1^{st}$ to $239^{th}$ amino acids of the amino sequence of SEQ ID NO. 2.

10 Claims, 9 Drawing Sheets

FIG. 3
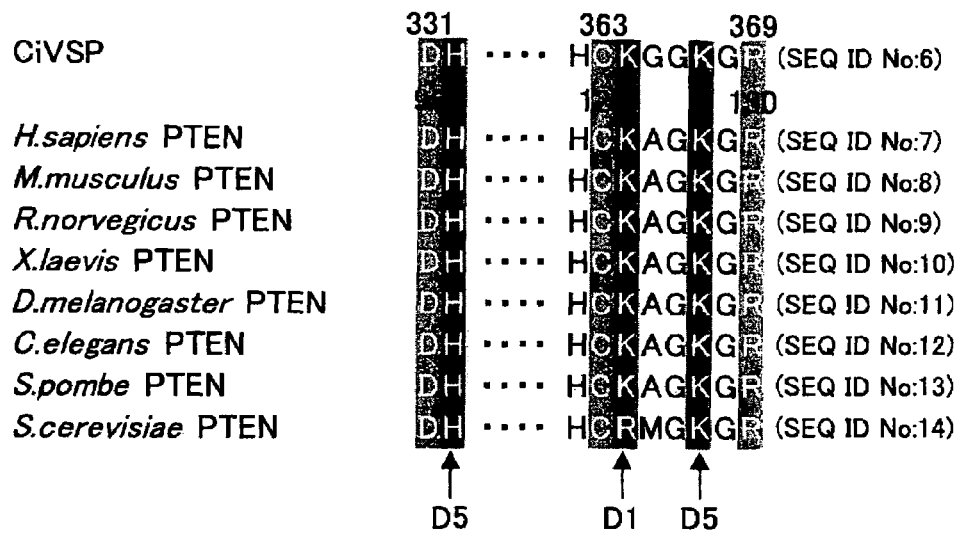
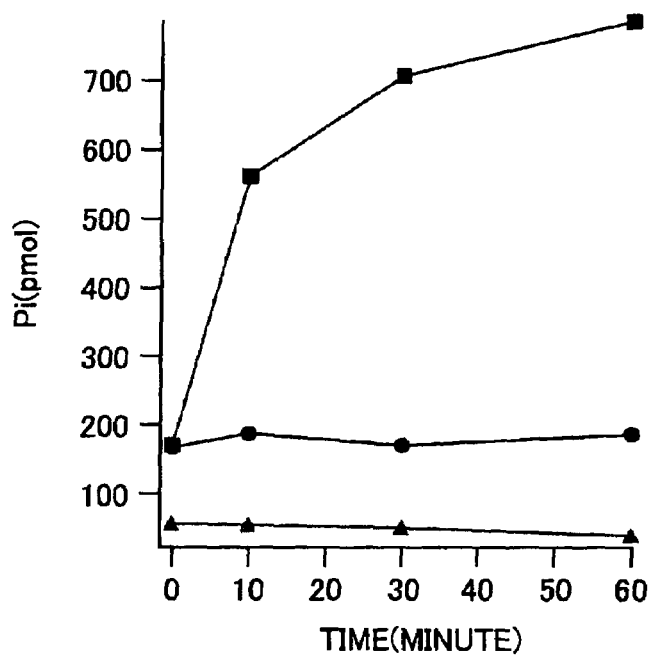

FIG. 6
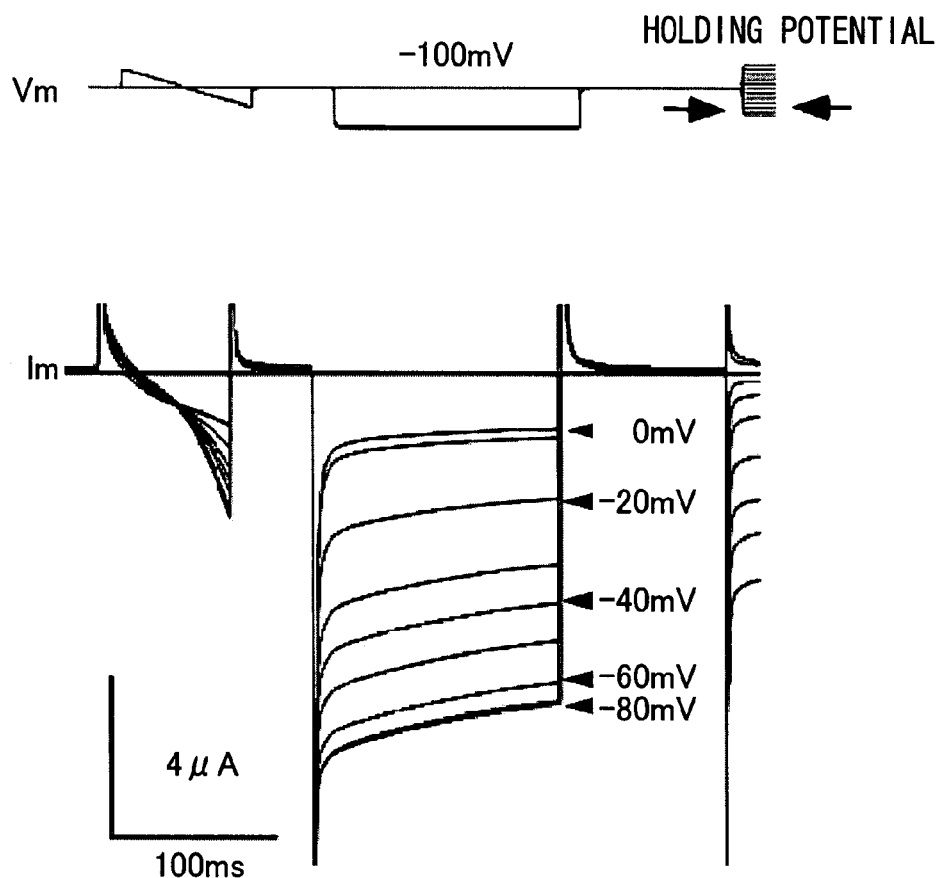
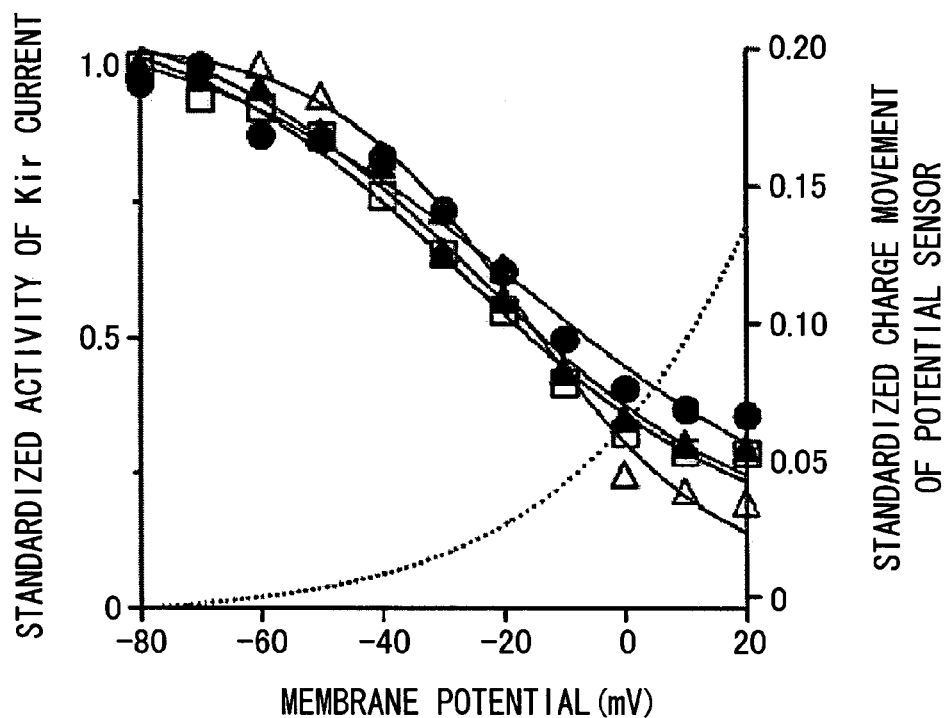

FIG. 8
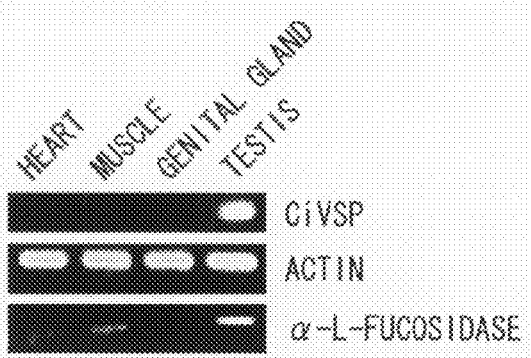
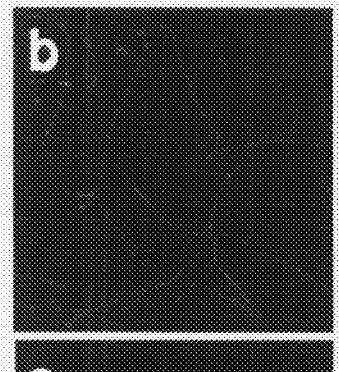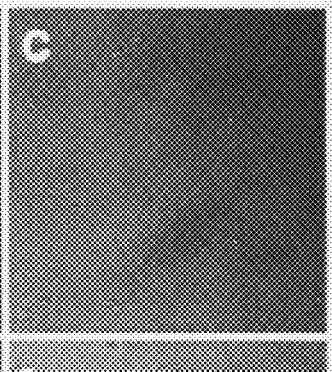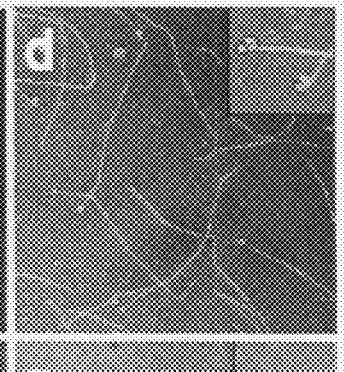
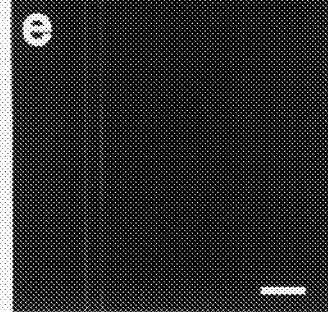
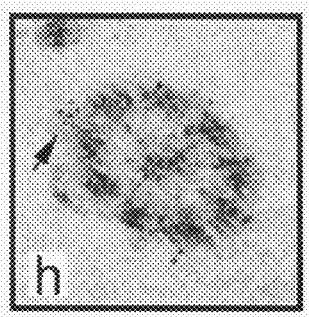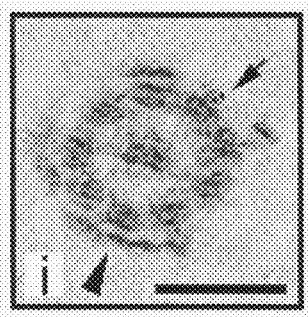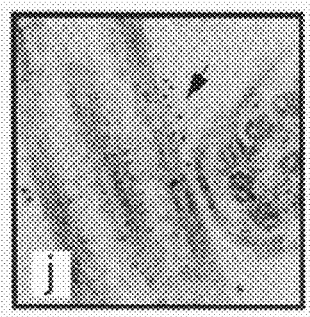

ION CHANNEL-LIKE POLYPEPTIDE AND USE THEREOF

TECHNICAL FIELD

The present invention relates to a single polypeptide that without any direct ion flow, is capable of converting electrical signals to chemical signals.

BACKGROUND ART

Ion channels reside in a cell membrane to control crossing of ions into the cell. Specifically, ion channels have a structure spanning the cell membrane, and open and close on various stimulations to bring ions into and out of the cell. The ion channels therefore constitute one class of molecules that elicit important biological reactions such as muscle contraction, release of neurotransmitters, and secretion of insulin. For example, the electrical signal transmission in nerve cells requires sodium channels or potassium channels. The potassium channels are essential for muscle contraction. Some of the different forms of ion channels are potential-dependent ion channels, which open and close according to a potential difference across the cell membrane, and receptor-activated ion channels, which open and close in response to binding of a ligand forming a complex with the receptor.

The inventors of the present invention have analyzed ion channel-mediated electrical activity using Ascidiacea, which is a member of Protochordata.

Ascidiacea belongs to Urochordata, and is a member of Chordata as are cephalochordates (for example, lancelets) and vertebrates (for example, frogs, humans). Unlike vertebrates, the chordate Ascidiacea does not have any redundant genes, preserving the basic form of chordates before gene redundancy. The tadpole larva of Ascidiacea has the simplest (original) form of organization among the chordates. This makes the chordate Ascidiacea the most suitable model animal for elucidation of development mechanism of vertebrates in general including humans. It is therefore anticipated that genes expressed in Ascidiacea will be applicable to medicine such as gene therapy and regenerative medicine, and various other fields including environment and food.

The inventors have previously reported a gene expression profile in the tailbud embryos of Ciona intestinalis (see Non-Patent Publication 1, for example).

Further, the inventors have performed EST (expressed sequence tag) analysis for 76,920 genes on the 3' sequence and 76,250 genes on the 5' sequence, concerning mRNA of genes expressed in a fertilized egg, cleaving embryos, tailbud embryos, larva, juvenile, or sperm of Ciona intestinalis. Expression of 5,000 genes selected from these genes was then examined by in situ hybridization. It was found as a result that about 500 genes were specifically expressed in the tailbud embryos, larva, or tissues or organs of juvenile. Among these genes, the entire base sequences of the mRNA (cDNA) of 261 genes were determined. (See Patent Publication 1, for example.)

Further, the inventors have performed EST analysis for about 23,000 genes on the 3' sequence and about 23,000 genes on the 5' sequence, concerning mRNA of genes expressed in the tailbud embryos and larva of Ciona intestinalis. Expression of about 3,000 genes selected from genes was examined by in situ hybridization. It was found as a result that about 200 genes were expressed in the nervous system (central nervous system or peripheral nervous system) of Ascidiacea. Among these genes, the entire base sequences of mRNA (cDNA) of 108 genes were determined. (See Patent Publication 2, for example.)

[Patent Publication 1]
Japanese Laid-Open Patent Publication No. 2004-57129 (published on Feb. 26, 2004)

[Patent Publication 2]
Japanese Laid-Open Patent Publication No. 2004-57127 (published on Feb. 26, 2004)

[Non-Patent Publication 1]
Development 128, 2893-2904 (2001)

In ion channel research, there has been established an experimental system in which ion channels, expressed for example in the oocyte of Xenopus laevis by a gene introducing technique are analyzed by techniques in electrophysiology. Such an experimental system is used to examine functions and control mechanism of ion channels, or influence of drugs on ion channel activity.

In order to examine influence of drugs on ion channels, it is generally required to capture a minute current that is generated by the movement of ions in and out of the cell. Measurement of cell membrane voltage from the cell conventionally requires a direct electrical measurement or a quantitative analysis using a voltage-sensitive pigment. However, it has been difficult with these techniques to obtain information concerning local membrane potential of the cell. Particularly, analysis has been impossible on materials of a small structure, such as sperm, to which the electrophysiological techniques are difficult to apply. Further, the experiment requires a skilled technique and is laborious.

Further, the screening techniques used in the research of enzymes and receptors are not directly applicable to ion channel research. This has slowed the development of drugs that involve ion channels. In fact, the only drugs that are known to act on ion channels are, for example, calcium antagonists available as hypotensive drugs, and local anesthetics.

Despite a wide range of studies that have been made on relations between physiological activity of organisms and ion channel molecules. Not all channel-like proteins have been identified and many questions remain unanswered. It is therefore useful to comprehensively analyze channel functions in simple organisms, from the genomic level to organism level.

DISCLOSURE OF INVENTION

In order to understand physiological phenomena based on ion channel molecules, the inventors of the present invention conducted a comprehensive study of ion channel genes in the genome sequence of Ciona intestinalis, which is an Urochordata belonging to Protochordata. The repertoire of ion channel molecular species was compared with those of Drosophila melanogaster, human, or balloon fish. As a result, the inventors found a gene that had a significant level of homology to the potential-dependent sodium channel. The protein encoded by this gene is a novel single membrane protein that without the need of any direct ion flow, is capable of converting electrical signals to chemical signals. No membrane protein is known that exhibits such properties. The inventors accomplished the present invention based on the finding that the novel membrane protein had a specified domain capable of independently functioning as a potential sensor and another domain exhibiting a phosphatase activity.

Specifically, a polypeptide according to the present invention is a polypeptide capable of functioning as a potential sensor, consisting of:

(a) 1st to 239th amino acids of the amino acid sequence of SEQ ID NO: 2; or (b) 1st to 239th amino acids of the amino acid sequence of SEQ ID NO: 2 with a deletion, insertion, substitution, or addition of one or several amino acids.

A polypeptide according to the present invention is a polypeptide capable of functioning as a potential sensor, encoded by:

(a) a polynucleotide consisting of 1st to 717th bases of the base sequence of SEQ ID NO: 1; or (b) a polynucleotide consisting of 1st to 717th bases of the base sequence of SEQ ID NO: 1 with a deletion, insertion, substitution, or addition of one or several bases.

A polypeptide according to the present invention is a polypeptide capable of functioning as a potential sensor, encoded by:

(a) a polynucleotide consisting of 1st to 717th bases of the base sequence of SEQ ID NO: 1; or (b) a polynucleotide that hybridizes under stringent conditions with a polynucleotide consisting of a base sequence complementary to the 1st to 717th bases of the base sequence of SEQ ID NO: 1.

A polypeptide according to the present invention is a polypeptide capable of functioning as a potential sensor, encoded by:

(a) a polynucleotide consisting of 1st to 717th bases of the base sequence of SEQ ID NO: 1; or (b) a polynucleotide consisting of a base sequence that is at least 80% identical to the base sequence complementary to the 1st to 717th bases of the base sequence of SEQ ID NO: 1.

A polypeptide according to the present invention is a polypeptide capable of functioning as a potential sensor, consisting of:

(a) 1st to 255th amino acids of the amino acid sequence of SEQ ID NO: 2; or (b) 1st to 255th amino acids of the amino acid sequence of SEQ ID NO: 2 with a deletion, insertion, substitution, or addition of one or several amino acids.

A polypeptide according to the present invention is a polypeptide capable of functioning as a potential sensor, encoded by:

(a) a polynucleotide consisting of 1st to 765th bases of the base sequence of SEQ ID NO: 1; or (b) a polynucleotide consisting of 1st to 765th bases of the base sequence of SEQ ID NO: 1 with a deletion, insertion, substitution, or addition of one or several bases.

A polypeptide according to the present invention is a polypeptide capable of functioning as a potential sensor, encoded by:

(a) a polynucleotide consisting of 1st to 765th bases of the base sequence of SEQ ID NO: 1; or (b) a polynucleotide that hybridizes under stringent conditions with a polynucleotide consisting of a base sequence complementary to the 1st to 765th bases of the base sequence of SEQ ID NO: 1.

A polypeptide according to the present invention is a polypeptide capable of functioning as a potential sensor, encoded by:

(a) a polynucleotide consisting of 1st to 765th bases of the base sequence of SEQ ID NO: 1; or (b) a polynucleotide consisting of a base sequence that is at least 80% identical to the base sequence complementary to the 1st to 765th bases of the base sequence of SEQ ID NO: 1.

A polynucleotide according to the present invention encodes a polypeptide of the present invention.

A polypeptide according to the present invention is a polypeptide capable of converting electrical signals to chemical signals without need of direct ion flow, the polypeptide consisting of:

(a) amino acids of the amino acid sequence of SEQ ID NO:2; or (b) amino acids of the amino acid sequence of SEQ ID NO:2 with a deletion, insertion, substitution, or addition of one or several amino acids.

A polypeptide according to the present invention is a polypeptide capable of converting electrical signals into chemical signals without need of direct ion flow, the polypeptide encoded by:

(a) a polynucleotide consisting of the base sequence of SEQ ID NO: 1; or (b) a polynucleotide consisting of the base sequence of SEQ ID NO: 1 with a deletion, insertion, substitution, or addition of one or several bases.

A polypeptide according to the present invention is a polypeptide capable of converting electrical signals into chemical signals without need of direct ion flow, the polypeptide encoded by:

(a) a polynucleotide consisting of the base sequence of SEQ ID NO: 1; or (b) a polynucleotide that hybridizes under stringent conditions with a polynucleotide consisting of a base sequence complementary to the base sequence of SEQ ID NO: 1.

A polypeptide according to the present invention is a polypeptide capable of converting electrical signals into chemical signals without need of direct ion flow, the polypeptide encoded by:

(a) a polynucleotide consisting of the base sequence of SEQ ID NO: 1; or (b) a polynucleotide consisting of a base sequence that is at least 80% identical to the base sequence complementary to the base sequence of SEQ ID NO: 1.

A polynucleotide according to the present invention is encoded by a polypeptide of the present invention.

A polypeptide according to the present invention includes 85th to 96th amino acids of the amino acid sequence of SEQ ID NO: 2.

It is preferable that a polypeptide according to the present invention be a fragment of a polypeptide consisting of amino acids of the amino acid sequence of SEQ IS NO: 2, and include the 85th to 96th amino acids of the amino acid sequence of SEQ ID NO: 2.

It is preferable that a polypeptide according to the present invention consist of the 85th to 96th amino acids of the amino acid sequence of SEQ ID NO: 2.

An oligonucleotide according to the present invention includes the 253rd to 286th bases of the base sequence of SEQ ID NO: 1.

An oligonucleotide according to the present invention is a fragment of a polynucleotide consisting of the base sequence of SEQ ID NO: 1, and includes the 253rd to 286th bases of the base sequence of SEQ ID NO: 1.

An oligonucleotide according to the present invention consists of the 253rd to 286th bases of the base sequence of SEQ ID NO: 1.

An antibody according to the present invention binds to a polypeptide of the present invention.

A polypeptide according to the present invention is a polypeptide having a phosphoinositide phosphatase activity, consisting of:

(a) 256th to 576th amino acids of the amino acid sequence of SEQ ID NO: 2; or (b) 256th to 576th amino acids of the amino acid sequence of SEQ ID NO: 2 with a deletion, insertion, substitution, or addition of one or several amino acids.

A polypeptide according to the present invention is a polypeptide having a phosphoinositide phosphatase activity, encoded by:

(a) a polynucleotide consisting of 766th to 1728th bases of the base sequence of SEQ ID NO: 1; or (b) a polynucleotide consisting of 766th to 1728th bases of the base sequence of SEQ ID NO: 1 with a deletion, insertion, substitution, or addition of one or several bases.

A polypeptide according to the present invention is a polypeptide having a phosphoinositide phosphatase activity, encoded by:

(a) a polynucleotide consisting of 766th to 1728th bases of the base sequence of SEQ ID NO: 1; or (b) a polynucleotide that hybridizes under stringent conditions with a polynucleotide consisting of a base sequence complementary to the 766th to 1728th bases of the base sequence of SEQ ID NO: 1.

A polypeptide according to the present invention is a polypeptide having a phosphoinositide phosphatase activity, encoded by:

(a) a polynucleotide consisting of 766th to 1728th bases of the base sequence of SEQ ID NO: 1; or (b) a polynucleotide consisting of a base sequence that is at least 80% identical to the base sequence complementary to the 766th to 1728th bases of the base sequence of SEQ ID NO: 1.

With a polypeptide according to the present invention as a novel potential sensor, changes in cytoplasmic local membrane potential can be captured by conversion into chemical or optical signals. This allows for analysis of physiological functions, and noninvasive measurement of membrane potential or noninvasive analysis of physiological functions in sperm, which has been impossible to analyze with a conventional electrophysiological approach using glass electrodes, and/or in bone cells, which are difficult to access.

Further, the present invention enables control of sperm motility, making it possible to avoid pregnancy, or treat or prevent infertility. It is known that a homologue of a gene encoding a polypeptide according to the present invention exists in mice, humans, and zebrafish, and that such homologous genes in humans constitute tumor marker molecules of liver cell carcinoma. Thus, by using a drug that causes a change in cell membrane potential, it would be possible to control malignancy of liver cell carcinoma.

A polynucleotide according to the present invention encodes a polypeptide of the present invention.

Additional objects, features, and strengths of the present invention will be made clear by the description below. Further, the advantages of the present invention will be evident from the following explanation in reference to the drawings.

BRIEF DESCRIPTION OF DRAWINGS

FIG. 3 shows that the cytoplasmic domain of Ci-VSP is phosphoinositide phosphatase, in which a compares amino acid sequence of the phosphatase active center of Ci-VSP with that of PTEN in various species; and b represents phosphoinositide phosphatase activity of the fusion protein of glutathione s-transferase and the phosphatase-like domain of Ci-VSP.

FIG. 6 is a diagram representing potential-dependence of phosphatase activity as probed with $K^+$ channel activities, in which a shows graphs of representative recordings of GIRK currents from oocytes expressing Ci-VSP and GIRK2; and b is a plot of current amplitudes of GIRK currents against membrane potential levels during intervals between test pulses.

FIG. 8 is a diagram representing localization of Ci-VSP in sperm tail, in which a shows RT-PCR of Ci-VSP transcripts in heart, somatic muscle, genital gland, and testis; b to g represent immunohistochemistry performed on *Ciona intestinals* sperm with a polyclonal antibody against the C-terminal peptide sequence of Ci-VSP; and h to k represent immunoelectron localization of Ci-VSP at plasma membrane of sperm flagella.

BEST MODE FOR CARRYING OUT THE INVENTION

The following will describe one embodiment of the present invention. It should be appreciated however that the present invention is not limited in any way by the following description.

First, description is made as to a polypeptide according to the present invention, and use thereof.

(1) Polypeptide

By the inventors of the present invention, cDNA of a novel gene weakly homologous to a potential-dependent sodium channel was cloned with RT-PCR, using young adults of *Ciona intestinalis*, and the full sequence of the entire coding region was determined. The protein encoded by this gene had four transmembrane domains followed by an enzyme-like domain. The four transmembrane segments of the protein were highly homologous to S4 segment of a potential-dependent channel in which several positively charged amino acid residues are periodically aligned with two intervening residues. Such a potential-dependent channel is known to move across the membrane in response to changes in membrane potential. Accordingly, the inventors of the present invention coined the term "Ci-VSP" (potential-sensor-containing protein) for the protein originating in *Ciona intestinalis*.

Figure 1:
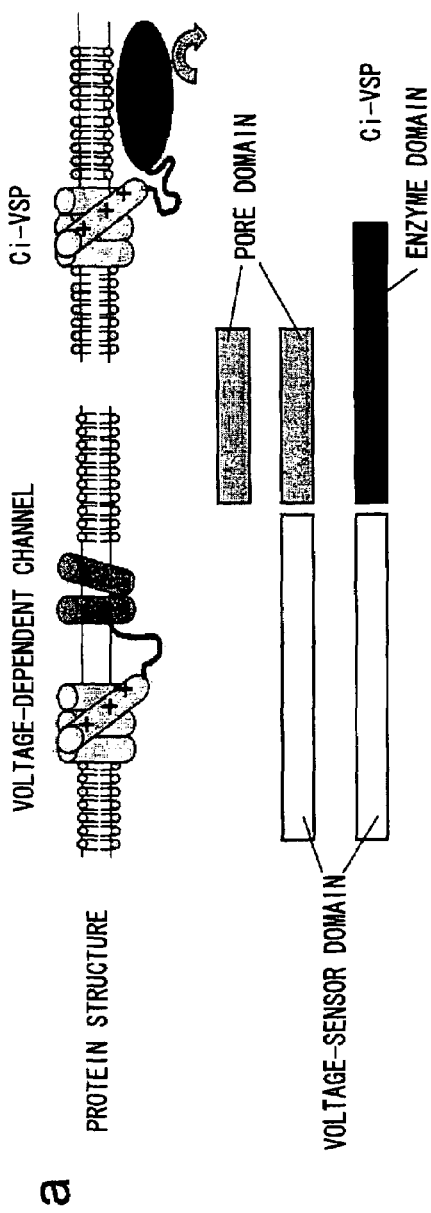
FIG. 1 shows the topology and primary structure of Ascidiacea protein Ci-VSP, in which a is a module structure of Ci-VSP polypeptide in comparison with potential-dependent, inward rectifier potassium channel; and b is the amino acid sequence of Ci-VSP polypeptide.

A polypeptide according to the present invention has a module structure and an amino acid sequence as shown in FIG. 1. As shown in FIG. 1a, a polypeptide according to the present invention has a module structure different from that of a potential-dependent, inward rectifier potassium channel. Further, as shown in FIG. 1b, a polypeptide according to the present invention includes four transmembrane segments (underlined), analogous to S1 to S4 segments of the potential-dependent channel, and a PTEN-like phosphatase domain (P-loop of the phosphatase domain is indicated by a square).

As described above, the Ci-VSP protein with the amino acid sequence of SEQ ID NO: 2 is a single protein that without the need of any direct ion flow, is capable of converting electrical signals to chemical signals. The Ci-VSP protein includes a specified domain (four transmembrane segments consisting of the $1^{st}$ to $239^{th}$ amino acids of the amino acid sequence of SEQ ID NO: 2) capable of independently functioning as a potential sensor, and a C-terminus domain (polypeptide consisting of the $256^{th}$ to $576^{th}$ amino acids of the amino acid sequence of SEQ ID NO: 2) exhibiting a phosphatase activity. These domains are linked together by a specific linker domain (polypeptide consisting of the $240^{th}$ to $255^{th}$ amino acids (SEQ ID NO: 5) of the amino acid sequence of SEQ ID NO: 2). By virtue of such a unique structure, a Ci-VSP polypeptide according to the present invention adjusts enzyme activity of the enzyme domain in response to a linker domain-mediated change in the electrical signal detected by the potential sensor module.

As used herein, the term "polypeptide" is used interchangeably with "peptide" or "protein." By a "fragment" of the polypeptide, it is intended a partial fragment of the polypeptide. A polypeptide according to the present invention may be isolated from a natural source, or may be produced by recombination. As used herein, the term "Ci-VSP polypeptide" is used interchangeably with "Ci-VSP protein," and is also referred to as Ci-VSP.

As used herein, an "isolated" polypeptide or protein is intended a polypeptide or protein obtained from the natural environment in which they occur. For example, recombinant polypeptides and proteins that are produced by being expressed in host cells can also be regarded as being "isolated," as with natural or recombinant polypeptides and proteins that are actually purified by any suitable technique.

A polypeptide according to the present invention includes products purified from nature, and products obtained by recombination using prokaryotic hosts or eukaryotic hosts (for example, *E. coli* cell, yeast cell, higher plant cell, insect cell, and mammalian cell). A polypeptide according to the present invention may be glycosylated host-dependently in the host used for the recombination procedure. Further, in some cases, a polypeptide according to the present invention may include a start modified-methionine residue as a result of a host-mediated process.

According to one aspect of the present invention, the invention provides a polypeptide with a VSP activity. As used herein, the "VSP activity" is intended the activity to convert electrical signals into chemical signals such as phosphorylation, without the need of direct ion flow.

In one embodiment, a polypeptide according to the present invention is preferably a polypeptide consisting of the amino acid sequence of SEQ ID NO: 2. In another embodiment, a polypeptide according to the present invention is preferably a mutant polypeptide consisting of the amino acid sequence of SEQ ID NO: 2 and having a VSP activity. As used herein, the "Ci-VSP polypeptide" is intended a polypeptide consisting of the amino acid sequence of SEQ ID NO: 2, or a mutant polypeptide thereof.

As used herein, the "polypeptide consisting of the amino acid sequence of SEQ ID NO: 2" is intended a polypeptide encoded by a polynucleotide consisting of the base sequence of SEQ ID NO: 1.

Such mutants include deletions, insertions, inversions, repeats, and type substitutions (for example, substituting one hydrophilic residue for another, but not strongly hydrophobic for strongly hydrophilic as a rule). Small changes or such "neutral" amino acid substitutions will generally have little effect on activity of the polypeptide.

It will be recognized in the art that some amino acid sequences of the polypeptide can be varied without significant effect on the structure or function of the polypeptide. It is also known that such a mutant with no significant structural or functional change occurs not only in artificially modified proteins but in nature as well.

The mutants preferably include those produced by substitutions, deletions, or additions of amino acid, which may be conservative or non-conservative. Especially preferred among these are silent substitutions, additions and deletions. Also especially preferred are conservative substitutions. These do not alter the VSP activity of a polypeptide of the present invention.

Typically seen as conservative substitutions are the replacements, one for another, among the aliphatic amino acids Ala, Val, Leu and Ile; interchange of the hydroxyl residues Ser and Thr, exchange of the acidic residues Asp and Glu, substitution between the amide residues Asn and Gln, exchange of the basic residues Lys and Arg and replacements among the aromatic residues Phe, Tyr.

As indicated in detail above, further guidance concerning which amino acid changes are likely to be phenotypically silent (i.e., are not likely to have a significant deleterious effect on a function) can be found in Bowie, J. U., et al., "Deciphering the Message in Protein Sequences: Tolerance to Amino Acid Substitutions," Science 247:1306-1310 (1990) (herein incorporated by reference).

It is easy for a person ordinary skill in the art to modify one or several amino acids in the amino acid sequence of a protein using a conventional technique. For example, by a conventional point mutation introducing method (mutagenesis), any base of a polynucleotide that encodes a protein can be mutated. Further, with a primer that is designed to correspond to an arbitrary site of a polynucleotide that encodes a protein, a deletion mutant or an addition mutant can be produced. Further, with the method described in the present invention, whether or not the mutant has desired VSP activities can easily be evaluated.

In one aspect of the present embodiment, a polypeptide according to the present embodiment is preferably a polypeptide with VSP activity, which consists of (a) the amino acids of the amino acid sequence of SEQ ID NO: 2; or (b) the amino acids of the amino acid sequence of SEQ ID NO: 2 with a deletion, insertion, substitution, or addition of one or several amino acids. Such a mutant polypeptide is not just limited to polypeptides that are artificially mutated by known mutant polypeptide producing methods, but may be isolated and purified from polypeptides that exist in nature.

In another aspect of the present embodiment, a polypeptide according to the present embodiment is preferably a polypeptide with VSP activity, which is encoded by:

(a) a polynucleotide consisting of the base sequence of SEQ ID NO: 1; or (b) a polynucleotide consisting of the base sequence of SEQ ID NO: 1 with a deletion, insertion, substitution, or addition of one or several bases.

In another aspect of the present embodiment, a polypeptide according to the present embodiment is preferably a polypeptide with VSP activity, which is encoded by:

(a) a polynucleotide consisting of the base sequence of SEQ ID NO: 1; or (b) a polynucleotide that hybridizes under stringent conditions with a polynucleotide consisting of a base sequence complementary to the base sequence of SEQ ID NO: 1.

Hybridization can be performed by conventional methods, for example, according to the procedure described in J. Sambrook et al. Molecular Cloning, A Laboratory Manual, 2nd Ed., Cold Spring Harbor Laboratory (1989). As a rule, the level of stringency increases (more difficult to hybridize) with increase in temperature and decrease in salt concentration, making it possible to obtain more homologous polynucleotides. Suitable hybridization temperatures vary depending on the base sequence or the length of base sequence. For example, when a DNA fragment of 18 bases encoding six amino acids is used as a probe, a hybridization temperature of 50° C. or below is preferable.

As used herein, "stringent hybridization conditions" is intended overnight incubation at 42° C. in a solution comprising: 50% formamide, 5×SSC (150 mM NaCl, 15 mM trisodium citrate), 50 mM sodium phosphate (pH7.6), 5×Denhardt's solution, 10% dextran sulfate, and 20 mg/ml denatured, sheared salmon sperm DNA, followed by washing the filters in 0.1×SSC at about 65° C. By a polynucleotide which hybridizes to a "portion" of a polynucleotide is intended a polynucleotide (either DNA or RNA) hybridizing to at least about 15 nucleotides (nt), and more preferably at least about 20 nt, still more preferably at least about 30 nt, and even more preferably longer than about 30 nt of the reference polynucleotide. Such a polynucleotide (oligonucleotide) which hybridizes to a "portion" of a polynucleotide is useful as a detection probe as discussed in more detail below.

In another aspect of the present embodiment, a polypeptide according to the present embodiment is preferably a polypeptide with VSP activity, which is encoded by:

(a) a polynucleotide consisting of the base sequence of SEQ ID NO: 1; or (b) a polynucleotide consisting of a base sequence at least 80% identical to, or more preferably at least 85%, 90%, 92%, 95%, 96%, 97%, 98%, or 99% identical to a base sequence complementary to the base sequence of SEQ ID NO: 1.

For example, by a "polynucleotide whose base sequence is at least 95% identical to a reference (query) base sequence encoding a polypeptide according to the present invention" is intended that the base sequence of the polynucleotide is identical to the reference sequence except that the polynucleotide sequence may include up to five point mutations (mismatches) per each 100 nucleotides (bases) of the reference base sequence encoding a polypeptide according to the present invention. In other words, to obtain a polynucleotide having a base sequence at least 95% identical to a reference base sequence, up to 5% of the bases in the reference sequence may be deleted or substituted with another base, or a number of bases up to 5% of the total bases in the reference sequence may be inserted into the reference sequence. These mutations of the reference sequence may occur at the 5' or 3' terminal positions of the reference base sequence or anywhere between those terminal positions, interspersed either individually among bases in the reference sequence or in one or more contiguous groups within the reference sequence. As described herein, the reference sequence may be a polynucleotide encoding the amino acid sequence of SEQ ID NO: 2, or a variant, derivative, or analog thereof.

As a practical matter, whether any particular nucleic acid molecule is at least 80%, 85%, 90%, 92%, 95%, 96%, 97%, 98% or 99% identical to, for instance, the base sequence of SEQ ID NO: 1 can be determined conventionally using known computer programs such as the Bestfit program (Wisconsin Sequence Analysis Package, Version 8 for Unix®, Genetics Computer Group, University Research Park, 575 Science Drive, Madison, Wis. 53711). Bestfit uses the local homology algorithm of Smith and Waterman, Advances in Applied Mathematics 2: 482-489 (1981), to find the best segment of homology between two sequences. When using Bestfit or any other sequence alignment program to determine whether a particular sequence is, for instance, 95% identical to a reference sequence according to the present invention, the parameters are set, of course, such that the percentage of identity is calculated over the full length of the reference base sequence and that gaps in homology of up to 5% of the total number of nucleotides in the reference sequence are allowed.

In a specific embodiment, the overall match between a reference (query) sequence (a sequence of the present invention) and a subject sequence, also referred to as a global sequence alignment, can be determined using the FASTDB computer program based on the algorithm of Brutlag et al. (Comp. App. Biosci. 6: 237-245 (1990)). Preferred parameters used in a FASTDB alignment of DNA sequences to calculate percent identity are: Matrix=Unitary, k-tuple=4, Mismatch Penalty=1, Joining Penalty=30, Randomization Group Length=0, Cutoff Score=1, Gap Penalty=5, Gap Size Penalty 0.05, Window Size=500 or the length of the subject base sequence, whichever is shorter. According to this specific embodiment, if the subject sequence is shorter than the QUERY sequence because of 5' or 3' deletions, not because of internal deletions, a manual correction must be made to the results. This is because the FASTDB program does not account for 5' and 3' truncations of the subject sequence when calculating percent identity. For subject sequences truncated at the 5' or 3' ends, relative to the query sequence, the percent identity is corrected by calculating the number of bases of the query sequence that are 5' and 3' of the subject sequence, which are not matched/aligned, as a percent of the total bases of the query sequence. Whether a nucleotide is matched/aligned is determined by results of the FASTDB sequence alignment. This percentage is then subtracted from the percent identity, calculated by the above FASTDB program using the specified parameters, to arrive at a final percent identity score. This corrected score is what is used for the purposes of the present embodiment. Only bases outside the 5' and 3' bases of the subject sequence, as displayed by the FASTDB alignment, which are not matched/aligned with the query sequence, are calculated for the purposes of manually adjusting the percent identity score. For example, a 90 base subject sequence is aligned to a 100 base query sequence to determine percent identity. The deletions occur at the 5' end of the subject sequence and therefore, the FASTDB alignment does not show a matched/alignment of the first 10 bases at 5' end. The 10 unpaired bases represent 10% of the sequence (number of bases at the 5' and 3' ends not matched/total number of bases in the query sequence) so 10% is subtracted from the percent identity score calculated by the FASTDB program. If the remaining 90 bases were perfectly matched the final percent identity would be 90%. In another example, a 90 base subject sequence is compared with a 100 base query sequence. This time the deletions are internal deletions so that there are no bases on the 5' or 3' of the subject sequence which are not matched/aligned with the query. In this case the percent identity calculated by FASTDB is not manually corrected. Once again, only bases 5' and 3' of the subject sequence which are not matched/aligned with the query sequence are manually corrected for. No other manual corrections are to made for the purposes of the present embodiment.

In another aspect of the present invention, the invention provides a polypeptide having activity as a potential sensor. As used herein, the "activity as a potential sensor" means the ability to detect electrical signals as a change in membrane potential, i.e., the activity to function as a potential sensor.

In one embodiment, a polypeptide according to the present invention is preferably a polypeptide consisting of the $1^{st}$ to $239^{th}$ amino acids of the amino acid sequence of SEQ ID NO: 2. A polypeptide according to the present embodiment may further include a polypeptide (linker region) consisting of the amino acid sequence of SEQ ID NO: 5.

In another embodiment, a polypeptide according to the present invention is preferably a mutant of the polypeptide consisting of the $1^{st}$ to $239^{th}$ amino acids of the amino acid sequence of SEQ ID NO: 2, and preferably has activity as a potential sensor. A polypeptide according to the present embodiment may further include a polypeptide consisting of the amino acid sequence of SEQ ID NO: 5.

A Ci-VSP polypeptide according to the present invention includes the $1^{st}$ to $239^{th}$ amino acids of the amino acid sequence of SEQ ID NO: 2, and therefore has not only the VSP activity but the activity as a potential sensor as well.

That is, it will be readily understood by a person ordinary skill in the art that a "polypeptide having activity as a potential sensor" according to the present invention includes a fragment of the polypeptide consisting of the amino acid sequence of SEQ ID NO:2, and includes a polypeptide having the $1^{st}$ to $239^{th}$ amino acids of the amino acid sequence of SEQ ID NO: 2, or a mutant thereof.

In another aspect of the present invention, the invention provides a polypeptide having phosphoinositide phosphatase activity. As used herein, the "phosphatase activity" refers to activity of phosphatase using phosphorylated phosphatidylinositol as a substrate.

In one embodiment of the present invention, a polypeptide according to the present invention is preferably a polypeptide consisting of the $256^{th}$ to $576^{th}$ amino acids of the amino acid sequence of SEQ ID NO: 2.

In another embodiment of the present invention, a polypeptide according to the present invention is preferably a mutant of the polypeptide consisting of the $256^{th}$ to $576^{th}$ amino acids of the amino acid sequence of SEQ ID NO: 2, and preferably has activity as a potential sensor.

A Ci-VSP polypeptide according to the present invention includes the $256^{th}$ to $576^{th}$ amino acids of the amino acid sequence of SEQ ID NO: 2, and therefore has not only the VSP activity but phosphatase activity as well. That is, it will be readily understood by a person ordinary skill in the art the a polypeptide having "phosphatase activity" according to the present invention includes a fragment of the polypeptide consisting of the amino acid sequence of SEQ ID NO: 2, and includes a polypeptide consisting of the $256^{th}$ to $576^{th}$ amino acids of the amino acid sequence of SEQ ID NO: 2, or a mutant thereof.

The linker region, which is the polypeptide consisting of the amino acid sequence of SEQ ID NO: 5, is important for the regulation of enzyme module's enzyme activity that is effected according to changes in electrical signals detected by the potential sensor module. With the linker region, the activity of a new enzyme domain can be regulated according to changes in electrical signals detected by the potential sensor module, even when the enzyme module of the Ci-VSP polypeptide is replaced with an enzyme domain other than the phosphatase domain.

A polypeptide according to the present invention has been described based on a polypeptide having VSP activity, potential sensor activity, or phosphatase activity. In another aspect, the invention provides a polypeptide having an amino acid sequence of an epitope-bearing portion of the polypeptide described herein. A polypeptide having an amino acid sequence of an epitope-bearing portion of a polypeptide according to the present invention includes a polypeptide portion having at least 6, 7, 8, 9, or 10 amino acids, as well as a polypeptide of an epitope-bearing portion of any length up to and including the full length of the amino acid sequence of a polypeptide according to the present invention encoded by the base sequence of SEQ ID NO: 1.

The present invention also provides an epitope-bearing peptide of a polypeptide according to the present invention. As described herein, a polypeptide of the present invention is immunogenic. An epitope portion of a protein that elicits an antibody response of a polypeptide of the present invention can be identified by methods known in the art. For instance, Geysen, et al. (1984) discloses a procedure for rapid concurrent synthesis on solid supports of hundreds of peptides of sufficient purity to react in an enzyme-linked immunosorbent assay. Interaction of synthesized peptides with antibodies is then easily detected without removing them from the support. In this manner a peptide bearing an immunogenic epitope of a desired protein may be identified routinely by one of ordinary skill in the art. For instance, the immunologically important epitope in the coat protein of foot-and-mouth disease virus was located by Geysen et al. supra with a resolution of seven amino acids by synthesis of an overlapping set of all 208 possible hexapeptides covering the entire 213 amino acid sequence of the protein. Then, a complete replacement set of peptides in which all 20 amino acids were substituted in turn at every position within the epitope were synthesized, and the particular amino acids conferring specificity for the reaction with antibody were determined. Thus, peptide analogs of the epitope-bearing peptides of the invention can be made routinely by this method. U.S. Pat. No. 4,708,781 to Geysen (1987) further describes this method of identifying a peptide bearing an immunogenic epitope of a desired protein.

An "immunogenic epitope" is defined as a part of a protein that elicits an antibody response when the whole protein is the immunogen. These immunogenic epitopes are believed to be confined to a few loci on the molecule. On the other hand, a region of a protein molecule to which an antibody can bind is defined as an "antigenic epitope." The number of immunogenic epitopes of a protein generally is less than the number of antigenic epitopes. See, for instance, Geysen, H. M., et al. (1984), Proc. Natl. Acad. Sci. USA 81: 3998-4002 (1984).

Antigenic epitope-bearing peptides according to the invention are therefore useful to raise antibodies, including monoclonal antibodies, that bind specifically to a polypeptide of the invention. Thus, a high proportion of hybridomas obtained by fusion of spleen cells from donors immunized with an antigen epitope-bearing peptide generally secrete antibody reactive with the native protein. The antibodies raised by antigenic epitope-bearing peptides are useful to detect the mimicked protein, and antibodies to different peptides may be used for tracking the fate of various regions of a protein precursor which undergoes post-translational processing. The peptides and anti-peptide antibodies may be used in a variety of qualitative or quantitative assays for the mimicked protein, for instance in competitive assays since it has been shown that even short peptides (e.g., about 9 amino acids) can bind and displace the larger peptides in immunoprecipitation assays (for instance, Wilson, et al., Cell 37:767-778 (1984) p. 777). The anti-peptide antibodies of the invention also are useful for purification of the mimicked protein, for instance, by adsorption chromatography using methods well known in the art.

Antigenic epitope-bearing peptides of the invention designed according to the above guidelines preferably contain a sequence of at least seven, more preferably at least nine and most preferably between about 15 to about 30 amino acids contained within the amino acid sequence of a polypeptide of the invention. However, peptides or polypeptides comprising a larger portion of an amino acid sequence of a polypeptide of the invention, containing about 30 to about 50 amino acids, or any length up to and including the entire amino acid sequence of a polypeptide of the invention, also are considered epitope-bearing peptides of the invention and also are useful for inducing antibodies that react with the mimicked protein. Preferably, the amino acid sequence of the epitope-bearing peptide is selected to provide substantial solubility in aqueous solvents (i.e., the sequence includes relatively hydrophilic residues and highly hydrophobic sequences are preferably avoided); and sequences containing proline residues are particularly preferred.

Preferably, a polypeptide according to the present invention includes the $85^{th}$ to $96^{th}$ amino acids of the amino acid sequence of SEQ ID NO: 2. More preferably, a polypeptide according to the present invention includes a fragment of a polypeptide having the amino acid sequence of SEQ ID NO: 2, or a mutant of such a polypeptide, and includes the $85^{th}$ to $96^{th}$ amino acids of the amino acid sequence of SEQ ID NO: 2. Most preferably, a polypeptide according to the present invention consists of the $85^{th}$ to $96^{th}$ amino acids of the amino acid sequence of SEQ ID NO: 2.

A polypeptide according to the present invention is not particularly limited as long as it is made up of amino acids bonded together by peptide bonding. A polypeptide according to the present invention may be a complex polypeptide that includes a non-polypeptide structure. As used herein, the "non-polypeptide structure" refers to a sugar chain or an isoprenoid group, for example. However, the meaning of the term is not particularly limited.

A polypeptide according to the present invention may include an additional polypeptide. An example of an additional polypeptide is an epitope-labeled polypeptide such as His, Myc, or Flag.

A polypeptide according to the present invention may be obtained by introducing a coding polynucleotide of a polypeptide according to the present invention into a host cell and expressing it in the host cell. Alternatively, a polypeptide according to the present invention may be isolated and purified from cells, tissues, and the like.

In another embodiment, a polypeptide according to the present invention may be expressed in a modified form, such as a fusion protein. For instance, a region of additional amino acids of polypeptide according to the present invention, particularly charged amino acids, may be added to the N- or C-terminus of the polypeptide to improve stability and persistence in the host cell, during purification, or during subsequent handling and storage.

A polypeptide according to the present embodiment may be fused at the N- or C-terminus to a tag label (tag sequence or marker sequence), such as a sequence encoding a peptide which facilitates purification of the fused polypeptide. Such sequences may be removed prior to final preparation of the polypeptide. In certain preferred embodiments of this aspect of the invention, the tagged amino acid sequence is a hexa-histidine peptide, such as the tag provided in a pQE vector (Qiagen, Inc.), among others, many of which are publicly/commercially available. As described in Gentz et al., Proc. Natl. Acad. Sci. USA 86:821-824 (1989) (incorporated herein by reference), for instance, hexa-histidine provides for convenient purification of the fusion protein. The "HA" tag is another peptide useful for purification which corresponds to an epitope derived from the influenza hemagglutinin (HA) protein, which has been described by Wilson et al., Cell 37: 767 (1984) (incorporated herein by reference). As discussed below, other such fusion proteins include a polypeptide according to the present embodiment, or a fragment thereof, fused to Fc at the N- or C-terminus.

In another embodiment, a polypeptide according to the present invention may be obtained by recombination, as described below.

Recombination may be performed by methods known in the art, using vectors and cells described below, for example.

As described thus far, a polypeptide according to the present invention is a polypeptide with VSP activity, and at least includes the amino acid sequence of SEQ ID NO: 2 or a mutant sequence thereof with the maintained activity, or a polypeptide according to the present invention is an epitope-bearing polypeptide of the polypeptide. Further, a polypeptide according to the present invention includes a polypeptide with activity as a potential sensor, at least consisting of the $1^{st}$ to $239^{th}$ amino acids of the amino acid sequence of SEQ ID NO: 2 or a mutant sequence thereof with the maintained activity, or a polypeptide according to the present invention includes a polypeptide with phosphatase activity, and at least consisting of the $256^{th}$ to $576^{th}$ amino acids of the amino acid sequence of SEQ ID NO: 2 or a mutant sequence thereof with the maintained activity. That is, it should be appreciated that the present invention also includes a polypeptide in which the polypeptide is linked to any amino acid sequence with specific functionalities (for example, tag). The polypeptide and any amino acid sequence with specific functionalities (for example, tag) may be linked together with a suitable linker that does not inhibit the respective functions of these peptides. However, in order to exhibit VSP activity, the linker peptide is preferably a polypeptide consisting of the amino acid sequence of SEQ ID NO: 5.

In short, an object of the present invention is to provide a polypeptide having VSP activity, potential sensor activity, or phosphatase activity; or an epitope-bearing polypeptide of the polypeptide. As such, a polypeptide according to the present invention is not bound to the specific methods of producing polypeptides described above. It should therefore be appreciated that the technical scope of the present invention also encompasses a polypeptide having VSP activity, potential sensor activity, or phosphatase activity; or an epitope-bearing polypeptide of the polypeptide, which is produced by other methods.

(2) Polynucleotide or Oligonucleotide

In one aspect of the present invention, the invention provides a polynucleotide encoding a polypeptide having VSP activity, or a fragment of such a polynucleotide. In another aspect, the invention provides a polynucleotide encoding a polypeptide having activity as a potential sensor, or a fragment of such a polynucleotide. In yet another aspect, the present invention provides a polynucleotide encoding a polypeptide having phosphatase activity, or a fragment of such a polynucleotide.

As used herein, the term "polynucleotide" is used interchangeably with "gene", "nucleic acid," or "nucleic acid molecule," and a collection of nucleotides is intended. As used herein, "base sequence" is used interchangeably with "nucleic acid sequence" or "nucleotide sequence," and it is represented by a sequence of deoxyribonucleotides (A, G, C, and T). Further, by a "polynucleotide having the base sequence of SEQ ID NO: 1, or a fragment thereof" is intended a polynucleotide having the sequence of deoxynucleotides A, G, C, and/or T of SEQ ID NO: 1, or a fragment thereof.

A polynucleotide according to the present invention may be in the form of RNA (for example, mRNA) or DNA (for example, cDNA or genomic DNA). The DNA may be double stranded or single stranded. The single strand DNA or RNA may be a coding strand (also known as a sense strand) or a non-coding strand (also known as an anti-sense strand).

A polynucleotide according to the present invention may be fused with a polynucleotide or oligonucleotide encoding the tag label (tag sequence or marker sequence) at in 5' or 3' region. As used herein, the term "oligonucleotide" refers to a molecule of several to several ten nucleotides, and it is used interchangeably with "polynucleotide." The oligonucleotide is denoted by the number of nucleotides it contains. For example, the term dinucleotide (dimmer) or trinucleotide (trimer) is used to refer to oligonucleotides of short sequences, whereas long oligonucleotides are referred to as 30 mers or 100 mers. The oligonucleotide may be produced as a fragment of a polynucleotide, or alternatively chemically synthesized.

An oligonucleotide according to the present invention is a fragment of at least 12 nt (nucleotides), preferably about 15 nt, more preferably at least about 20 nt, further preferably at least about 30 nt, or even more preferably at least about 40 nt. By "a fragment at least 20 nt in length" is intended fragments which include 20 or more contiguous bases in the nucleotide sequence of SEQ ID NO: 1, for example. Since the base sequence of SEQ ID NO: 1 is provided by an embodiment of the present invention, generating such DNA fragments based on SEQ ID NO: 1 would be routine to the skilled artisan. For example, restriction endonuclease cleavage or shearing by sonication could easily be used to generate fragments of various sizes. Alternatively, such fragments could be generated synthetically. Suitable fragments (oligonucleotides) are synthesized with the Synthesizer Type 392 of Applied Biosystems Incorporated (ABI, 850 Lincoln Center Dr., Foster City, Calif. 94404).

In another aspect, an oligonucleotide according to the present invention preferably hybridizes with a polynucleotide consisting of the base sequence of SEQ ID NO: 1 or a mutant thereof. "Mutants" can occur naturally, such as a natural allelic variant. By an "allelic variant" is intended one of several alternate forms of a gene occupying a given locus on a chromosome of an organism. Non-naturally occurring variants can be produced, e.g., using art-known mutagenesis techniques.

In another aspect, the present invention provides a fragment of a polynucleotide consisting of the base sequence of SEQ ID NO: 1, or a fragment of a mutant of such a polynucleotide, or an oligonucleotide having a complementary sequence to such a fragment.

It will be apparent for a person ordinary skill in the art that a polynucleotide according to the present invention may be used as a primer for polymerase chain reaction (PCR) to produce a polypeptide of the present invention, even when an oligonucleotide according to the present invention does not encode a polypeptide having VSP activity, potential sensor activity, or phosphatase activity. When an oligonucleotide according to the present invention does not encode a polypeptide of the present invention, the oligonucleotide has the following applications: (1) isolation of Ci-VSP gene or its alleles in cDNA libraries, or of splicing variants; (2) in situ hybridization (e.g., "FISH") for metaphase chromosomal spreads to provide precise chromosomal location of Ci-VSP gene, as described in Verma et al., Human Chromosomes: a manual of Basic Techniques, Pergamon Press, New York (1988); and (3) a Northern blot analysis for detecting Ci-VSP mRNA expression in specific tissues.

A polynucleotide or oligonucleotide according to the present invention includes not only double-stranded DNA but also single-stranded DNA or RNA, or a sense strand or anti-sense strand, constituting the double strand. A polynucleotide or oligonucleotide according to the present invention may be used as a tool for gene expression manipulations by anti-sense RNA mechanism. By the anti-sense RNA technique, a reduction of gene product derived from endogenous genes is observed. A polynucleotide or oligonucleotide according to the present invention may include sequences such as a sequence of untranslated region (UTR), or a vector sequence (including expression vector sequence).

A polynucleotide or oligonucleotide according to the present invention can be obtained by various kinds of known methods for isolating DNA fragments containing a polynucleotide or oligonucleotide according to the present invention. For example, a probe is prepared that specifically hybridizes with a portion of the base sequence of a polynucleotide of the present invention, and a genomic DNA library or cDNA library is screened with the probe. In this way, a polynucleotide or oligonucleotide of the present invention can be obtained. As the probe, a polynucleotide (oligonucleotide) can be used that specifically hybridizes with at least a portion of the base sequence, or its complementary sequence, of a polynucleotide of the present invention. A natural polynucleotide is a non-limiting example of a polynucleotide that is selected by such hybridization.

Alternatively, a polynucleotide according to the present invention can be obtained using PCR. The PCR amplification method is performed with, for example, the step of preparing primers from the 5' end and/or 3' end of the sequence, or its complementary sequence, of the cDNA of a polynucleotide according to the present invention; and the step of PCR amplifying the DNA with the primers, using the genomic DNA (or cDNA) as a template for example. In this way, DNA fragments containing a polynucleotide according to the present invention can be obtained in mass quantity.

A source of a polynucleotide according to the present invention is not particularly limited, but it is preferably a biological material such as the testicular tissue of adult *Ciona intestinalis*. As used herein, a "biological material" refers to a biological sample (tissue sample or cell sample obtained from living organisms).

A polynucleotide or oligonucleotide according to the present invention, by detecting a polynucleotide with which it hybridizes, may be used to easily detect organisms or tissues (including cells) expressing a polypeptide having VSP activity, potential sensor activity, or phosphatase activity.

A polynucleotide or oligonucleotide according to the present invention may be used as a hybridization probe that detects a polynucleotide encoding a polypeptide having VSP activity, potential sensor activity, or phosphatase activity, or as a primer for amplifying a polynucleotide encoding a polypeptide having VSP activity, potential sensor activity, or phosphatase activity. In this way, organisms or tissues expressing a polypeptide having VSP activity, potential sensor activity, or phosphatase activity can be easily detected. Preferably, an oligonucleotide according to the present invention consists of the base sequence of SEQ ID NO: 3 or 4. By using the oligonucleotide as an anti-sense oligonucleotide, expression of a polypeptide having VSP activity, potential sensor activity, or phosphatase activity can be inhibited in the organisms, or cells or tissues of the organisms.

In another aspect, the present invention provides a polynucleotide encoding an epitope-bearing polypeptide of a polypeptide having VSP activity, potential sensor activity, or phosphatase activity. Preferably, an oligonucleotide according to the present invention includes the $253^{rd}$ to $286^{th}$ bases of the base sequence of SEQ ID NO: 1. More preferably, an oligonucleotide according to the present invention is a fragment of a polynucleotide consisting of the base sequence of SEQ ID NO:1, and includes the $253^{rd}$ to $286^{th}$ bases of the base sequence of SEQ ID NO: 1. Most preferably, an oligonucleotide according to the present invention consists of the $253^{rd}$ to $286^{th}$ bases of the base sequence of SEQ ID NO: 1.

In short, an object of the present invention is to provide a polynucleotide encoding a polypeptide having VSP activity, potential sensor activity, or phosphatase activity; an oligonucleotide that hybridizes with the polynucleotide; or a polynucleotide encoding an epitope-bearing polypeptide of the polypeptide. As such, a polynucleotide or oligonucleotide according to the present invention is not bound to the specific methods of producing polynucleotides or oligonucleotides described above. It should therefore be appreciated that the technical scope of the present invention also encompasses a polynucleotide encoding a polypeptide having VSP activity, potential sensor activity, or phosphatase activity; or a polynucleotide encoding an epitope-bearing polypeptide of the polypeptide, which is produced by other methods.

(3) Use of a Polypeptide or Polynucleotide According to the Present Invention (A) Vector The present invention provides a vector used to produce a polypeptide according to the present invention. A vector according to the present invention is not particularly limited as long as it includes a polynucleotide encoding a polypeptide according to the present invention. A plasmid vector (pSP64, pBluescript, and the like) having a recognition sequence for RNA polymerase is preferable. An example is a recombinant expression vector to which cDNA of a polynucleotide encoding a polypeptide (may or may not include a signal sequence) having VSP activity, potential sensor activity, or phosphatase activity has been introduced. A method for producing the recombinant expression vector is not particularly limited. Methods using plasmids, phages, or cosmids may be used.

The vector is not limited to a specific type of vector, and those that can be expressed in host cells may be suitably selected. Specifically, according to the type of host cell, a suitable promoter sequence for reliable expression of a polynucleotide according to the present invention is selected, and a polynucleotide according to the present invention is incorporated in various kinds of plasmids to provide an expression vector.

An expression vector according to the present invention includes an expression control region (for example, a promoter, terminator, and/or replication origin), depending on the type of host to which it is introduced. As a promoter of an expression vector for bacteria, common promoters (for example, trc promoter, lac promoter) are used. Examples of a promoter for yeast include glyceraldehyde-3-phosphate dehydrogenase promoter and PH05 promoter. Examples of a promoter for fungi include amylase and trpC. As a promoter for animal cell host, virus promoters (for example, SV40 early promoter, SV40 later promoter) may be used. The expression vector may be produced by common techniques using restriction enzyme and/or ligase. Transformation of the host by the expression vector can also be performed using common techniques.

The transformed host by the expression vector is cultured, cultivated, or grown, and target proteins are collected and purified from the host using common techniques such as filtration, centrifugation, cell disruption, gel filtration chromatography, and ion exchange chromatography.

Preferably, the expression vector includes at least one selection marker. Examples of such markers include dihydrofolate reductase or neomycin resistant gene for eukaryotic cell culture, and tetracyclin resistant gene or ampicillin resistant gene for *E. coli* or other bacteria.

The selection marker allows for confirmation whether a polynucleotide according to the present invention has been introduced into the hose cell or successfully expressed in the host cell. Alternatively, a polypeptide according to the present invention may be expressed as a fusion polypeptide. For example, green fluorescent polypeptide GFP (green fluorescent protein) derived from *Aequorea victoria* may be used as a marker to express a polypeptide according to the present invention as a fusion polypeptide.

The type of host cell is not particularly limited, and various types of conventional cells may be suitably used. Specific examples include: bacteria such as *Escherichia coli*; yeasts such as *Saccharomyces cerevisiae* and *Schizosaccharomyces pombe*; nematodes such as *Caenorhabditis elegans*; oocytes of platanna (*Xenopus Laevis*); and animal cells (for example, CHO cells, COS cells, Bowes melanoma cells).

A method of introducing the expression vector into the host cell, i.e., transformation method is not particularly limited either. For example, various types of conventional methods such as an electroporation method, calcium phosphate method, a liposome method, and DEAE dextran method can be suitably used. When a polypeptide according to the present invention is expressed in insects for example, an expression system using baculovirus is used.

By introducing the polynucleotide into organisms or cells using a vector according to the present invention, expression of the polypeptide with VSP activity, potential sensor activity, or phosphatase activity is possible within the organisms or cells.

In short, a vector according to the present invention is an expression vector including at least a polynucleotide that encodes a polypeptide according to the present invention.

That is, an object of the present invention is to provide an expression vector including a polynucleotide encoding a polypeptide according to the present invention. As such, the present invention is not bound to the specific types of vectors and cells, or the specific methods of producing the vector or introducing the vector into cells described above. It should therefore be appreciated that the technical scope of the present invention also encompasses an expression vector that is obtained using vectors, and methods of producing vectors other than those described above.

(B) Transformant

The present invention provides a transformant to which a polynucleotide encoding a polypeptide having VSP activity, potential sensor activity, or phosphatase activity has been introduced. As used herein, the term "transformant" refers to not just cells, tissues, or organs but individual organisms themselves. The type of living organisms subject of transformation is not particularly limited. Various types of microorganisms, plants, and animals, described above in conjunction with the host cell may be used.

A transformant according to the present invention expresses therein a polypeptide having VSP activity, potential sensor activity, or phosphatase activity. It is preferable that a transformant according to the present invention stably express a polypeptide having VSP activity, potential sensor activity, or phosphatase activity. However, the expression may be transient.

In one embodiment, a transformant according to the present invention is obtained by introducing a vector of the present invention into an organism and expressing the polypeptide therein. Preferably, a transformant according to the present invention is a cell that stably expresses a polypeptide according to the present invention.

(C) Producing Method of Polypeptide

The present invention provides a method for producing a polypeptide according to the present invention. By a producing method of a polypeptide according to the present invention, a polypeptide having VSP activity, potential sensor activity, or phosphatase activity can be produced at low cost and under environmentally friendly conditions. Further, a producing method of a polypeptide according to the present invention can be used to easily produce a polypeptide having VSP activity, potential sensor activity, or phosphatase activity.

In one embodiment, a producing method of a polypeptide according to the present invention uses a vector of the present invention.

In one aspect of an embodiment of the present invention, a producing method of a polypeptide according to the present embodiment preferably uses a recombinant expression system using a living host. In using a recombinant expression system, a polynucleotide according to the present invention may be first incorporated in a recombinant expression vector, and then expressively introduced into a host by a known method. The polypeptide obtained by being translated in the host can then be purified. The recombinant expression vector may or may not be a plasmid as long as a target polynucleotide is introduced into the host. Preferably, a producing method of a polypeptide according to the present embodiment includes the step of introducing the vector into a host.

In introducing a foreign polynucleotide into a host, it is preferable that the expression vector has incorporated therein a promoter that becomes functional in the host and expresses the foreign polynucleotide. The method of purifying the recombinantly produced polypeptide varies depending on the type of host and properties of the polypeptide. However, a target polypeptide can be purified relatively easily with the use of a tag, for example.

In another embodiment, a producing method of a polypeptide according to the present invention purifies a polypeptide according to the present invention from cells or tissues in which a polypeptide according to the present invention is naturally or recombinantly expressed. A polypeptide according to the present invention is secreted from the cell in mature form, and therefore a polypeptide according to the present invention can be collected from the culture supernatant of the cells in which a polypeptide according to the present invention is naturally or recombinantly expressed. In such cases, a producing method of a polypeptide according to the present invention includes the step of collecting a culture supernatant. A producing method of a polypeptide according to the present embodiment may further include the step of purifying the polypeptide.

It is preferable that a producing method of a polypeptide according to the present invention further include the step of purifying the polypeptide from the cell or tissue extract containing a polypeptide of the present invention. The polypeptide purification step is preferably performed by first preparing a cell extract from cells or tissues by a known method (for example, centrifugating disrupted cells or tissues and collecting a soluble fraction), and purifying the polypeptide from the cell extract using a known method (for example, ammonium sulfate precipitation, ethanol precipitation, acid extraction, anion or cation exchange chromatography, phosphocellulose chromatography, hydrophobic interaction chromatography, affinity chromatography, hydroxyapatite chromatography, and lectin chromatography). The polypeptide purification step is not limited to this example however. High performance liquid chromatography (HPLC) is most preferably used for the purification.

In sum, an object of the present invention is to provide a method for producing a polypeptide having VSP activity, potential sensor activity, or phosphatase activity. It should therefore be appreciated that the technical scope of the present invention also encompasses a producing method including steps other than those described above.

(D) Antibody

The present invention provides an antibody that binds to a polypeptide of the present invention. Use of an antibody according to the present invention allows for a wide range of various assays, including detection of a polypeptide having VSP activity, potential sensor activity, or phosphatase activity. Further, a polypeptide having VSP activity, potential sensor activity, or phosphatase activity can be easily purified using an antibody according to the present invention.

In one embodiment, an antibody according to the present invention preferably binds to a polypeptide consisting of the amino acid sequence of SEQ ID NO: 2. More specifically, an antibody according to the present invention binds to a polypeptide which is a fragment of a polypeptide consisting of the amino acid sequence of SEQ ID NO: 2 and which includes the $85^{th}$ to $96^{th}$ amino acids of the amino acid sequence of SEQ ID NO: 2. Most preferably, an antibody according to the present invention binds to a polypeptide consisting of the $85^{th}$ to $96^{th}$ amino acids of the amino acid sequence of SEQ ID NO: 2.

An antibody according to the present invention may be elicited by a polypeptide, used as an antigen, that has been produced by any conventional means for making peptides, including recombinant means using a polynucleotide encoding the epitope-bearing peptide. For instance, the antigen, which is a short epitope-bearing amino acid sequence, may be fused to a larger polypeptide which acts as a carrier during recombinant production and purification, as well as during immunization to produce anti-peptide antibodies. Epitope-bearing peptides as antigens also may be synthesized using known methods of chemical synthesis.

The epitope-bearing peptides are used to induce an antibody of the present invention according to methods well known in the art (for instance, Chow, M., et al., Proc. Natl. Acad. Sci. USA 82:910-914; and Bittle, F. J., et al., J. Gen. Virol. 66:2347-2354 (1985)). Generally, animals may be immunized with free peptide; however, anti-peptide antibody titer may be boosted by coupling of the peptide to a macromolecular carrier, such as keyhole limpet hemacyanin (KLH) or tetanus toxoid. For instance, peptides containing cysteine may be coupled to carrier using a linker such as m-maleimidobenzoyl-N-hydroxysuccinimide ester (MBS), while other peptides may be coupled to carrier using a more general linking agent such as glutaraldehyde. Animals such as rabbits, rats and mice are immunized with either free or carrier-coupled peptides, for instance, by intraperitoneal and/or intradermal injection of emulsions containing about 100 μg peptide or carrier protein and Freund's adjuvant. Several booster injections may be needed, for instance, at intervals of about two weeks, to provide a useful titer of anti-peptide antibody which can be detected, for example, by ELISA assay using free peptide adsorbed to a solid surface. The titer of anti-peptide antibodies in serum from an immunized animal may be increased by selection of anti-peptide antibodies, for instance, by adsorption to the peptide on a solid support and elution of the selected antibodies according to methods well known in the art.

In a specific aspect, the present invention provides an antibody that inhibits functions of Ci-VSP polypeptide. Peptides of 10 to 15 amino acid residues are synthesized that respectively correspond to the $124^{th}$ to $134^{th}$ amino acids, the $145^{th}$ to $160^{th}$ amino acids, the $200^{th}$ to $214^{th}$ amino acids, and $215^{th}$ to $230^{th}$ amino acids of extracellular domains of S1 to S4 domains of Ci-VSP. Rabbits are immunized with these peptides and IgG fraction is purified from the serum. After VSP expression in the *Xenopus* oocyte system, ND96 solution supplemented with the antibody is administered to the cells. By examining whether there is inhibition of VSP functions before and after the administration, an antibody that inhibits functions of Ci-VSP can be produced.

(E) Screening Method and Pharmaceutical Composition

The present invention provides a method for screening for a compound regulating functions of Ci-VSP polypeptide, and a pharmaceutical composition (for example, medicament) containing such a compound. Results of an immunohistological staining using anti-Ci-VSP antibody revealed that the Ci-VSP polypeptide resided in the tail of sperm. It is envisaged that Ci-VSP, which changes enzyme activity based on membrane potential, controls sperm motility based on electrical signals.

A screening method of a compound that regulates functions of Ci-VSP polypeptide in sperm includes the steps of:

(I) forcing expression of VSP and GIRK channel in *Xenopus* oocytes;

(II) administering a candidate compound to the cells; and (III) detecting potential-dependent K channel activity or gate current.

To examine sperm motility, a medicament identified by the screening method is applied to isolated mouse sperm and changes in mobility are examined.

Specifically, mouse sperm is isolated to a Krebs-Ringer solution and diluted in a Krebs-Ringer solution containing 50 μM to 1 mM cAMP analog and 100 μM IMBX. After culturing for 5 to 180 minutes at 37° C. in a gas mixture of 5% $CO_2$ and 95% $O_2$, changes in motility of at least 500 sperms are examined with and without the drug in a vessel having a depth of 80 μm, using a sperm image analyzer (for example, the IVOS Sperm Analyzer of Hamilton-Thorne Research). The compound obtained by the screening method can be used to control motility of sperms, making it possible to avoid pregnancy, or treat or prevent infertility.

It is known that a homologue of a gene encoding a polypeptide according to the present invention exists in mice, humans, and zebrafish, and that such homologous genes in humans constitute tumor marker molecules of liver cell carcinoma. Thus, by using a drug that causes a change in cell membrane potential, it would be possible to control malignancy of liver cell carcinoma. A compound for controlling malignancy of cancer cell can be screened for according to the following scheme.

Liver cancer cells expressing human VSP gene are cultured at 37° C. in DMEM medium containing 10% serum. Expression of VSP gene is confirmed by RT-PCR reaction using human VSP-specific PCR primers. Total RNA is extracted from the human liver cancer cells, and cDNA is synthesized by reverse transcription from about 1 μg of RNA. PCR is run in 30 cycles consisting of 94° C. for 60 seconds, 55° C. for 45 seconds, and 72° C. for 60 seconds.

When the cells are 50% confluent, the medium in the dish is exchanged with medium containing Nicorandil (100 μM) or Diazoxide (0.1 mM), which is an activator of ATP-K channel. After the medium is exchanged, cells that have undergone apoptosis are counted over time using TUNEL method and trypan blue staining. Similar quantification is made under varying concentrations of Nicorandil or Diazoxide to establish a relation between apoptosis and concentration of the K channel activator.

A pharmaceutical composition according to the present invention may include a suitable pharmaceutically acceptable carrier, in addition to the pharmacologically active compound. The carrier includes a diluting agent and an auxiliary agent that facilitate processing of the active compound in pharmaceutically usable preparations. The pharmaceutically acceptable carrier used for a pharmaceutical composition according to the present invention can be suitably selected by a person ordinary skill in the art according to administration form or dosage form of the pharmaceutical composition.

In an orally administered form, the pharmaceutically acceptable carrier is, for example, starch, lactose, saccharose, mannitol, carboxylmethyl cellulose, corn starch, or inorganic salt. The orally administered drug may be prepared to include a binder, a disintegrant, a detergent, a lubricant, fluidity accelerator, a flavoring substance, a colorant, or a fragrant material.

In a non-orally administered form, an effective component of the present invention may be dissolved or suspended in a diluent such as distilled water for injection, a physiological saline, an aqueous solution of glucose, a vegetable oil for injection, a sesame oil, a nut oil, a soybean oil, a corn oil, propylene glycol, or polyethylene glycol, according to methods known in the art, and may be additionally supplemented as desired with a disinfectant, a stabilizing agent, an isotonic agent, a soothing agent, or the like.

A pharmaceutical composition according to the present invention may be manufactured according to methods known in the field of pharmaceuticals. The content of a pharmaceutically active compound in a pharmaceutical composition according to the present invention is not particularly limited as long as the active compound can be administered with the pharmaceutical composition in an administration range to be described later, taking into account such factors as form and method of administration.

A pharmaceutical composition according to the present invention may be administered in a suitable administration route according to form of drug. For example, a pharmaceutical composition according to the present invention may be conveniently administered orally, locally, intravenously, intraperitoneally, intramuscularly, subcutaneously, intranasally, or intracutaneously. For example, an injectable solution may be administered intravenously, intramuscularly, subcutaneously, or intracutaneously.

A dose of a pharmaceutical composition according to the present embodiment is not constant and is suitably set according to such factors as form of drug, method of administration, intended use, and age, body weight, and symptom of the subject to which the medicament is administered. Administration may be made either at once or in separate doses in a day, within a predetermined dose range.

(F) Method, Composition, and Kit for Ex Vivo Treatment

The present invention also provides a method, composition, and kit for treating a subject through ex vivo manipulation of cells originating in the subject. Results of an immunohistological staining using anti-Ci-VSP antibody revealed that the Ci-VSP polypeptide resided in the tail of sperm. It is envisaged that Ci-VSP, which changes enzyme activity based on membrane potential, controls sperm motility based on electrical signals. It is therefore possible, through manipulation of Ci-VSP gene in the subject sperm, to treat or prevent infertility caused by mutation in Ci-VSP.

For example, cells originating in a patient may be manipulated ex vivo using a polynucleotide (DNA or RNA) encoding a polypeptide, and the modified cells are put back to the patient to be treated by the polypeptide. Such methods are well known in the art and are deemed to be within the scope of those skilled in the art from the teachings herein. For example, the cells may be manipulated using a retrovirus plasmid vector including RNA that encodes a polypeptide according to the present invention.

Similarly, the cells may be manipulated, for example, in vivo according to procedures well known in the art, in order to express the polypeptide in vivo. For example, packaging cells are transformed with a retrovirus plasmid vector including RNA that encodes a polypeptide according to the present invention. Today, the packaging cells produce even infectious virus particles containing a target gene. The producer cells may be administered to a patient for in vivo manipulation of cells and in vivo expression of the polypeptide. These and other methods for administering a polypeptide according to the present invention are deemed to be within the scope of those skilled in the art from the teachings herein.

(G) Artificial Blood Vessel and/or Artificial Bone

Figure 9:
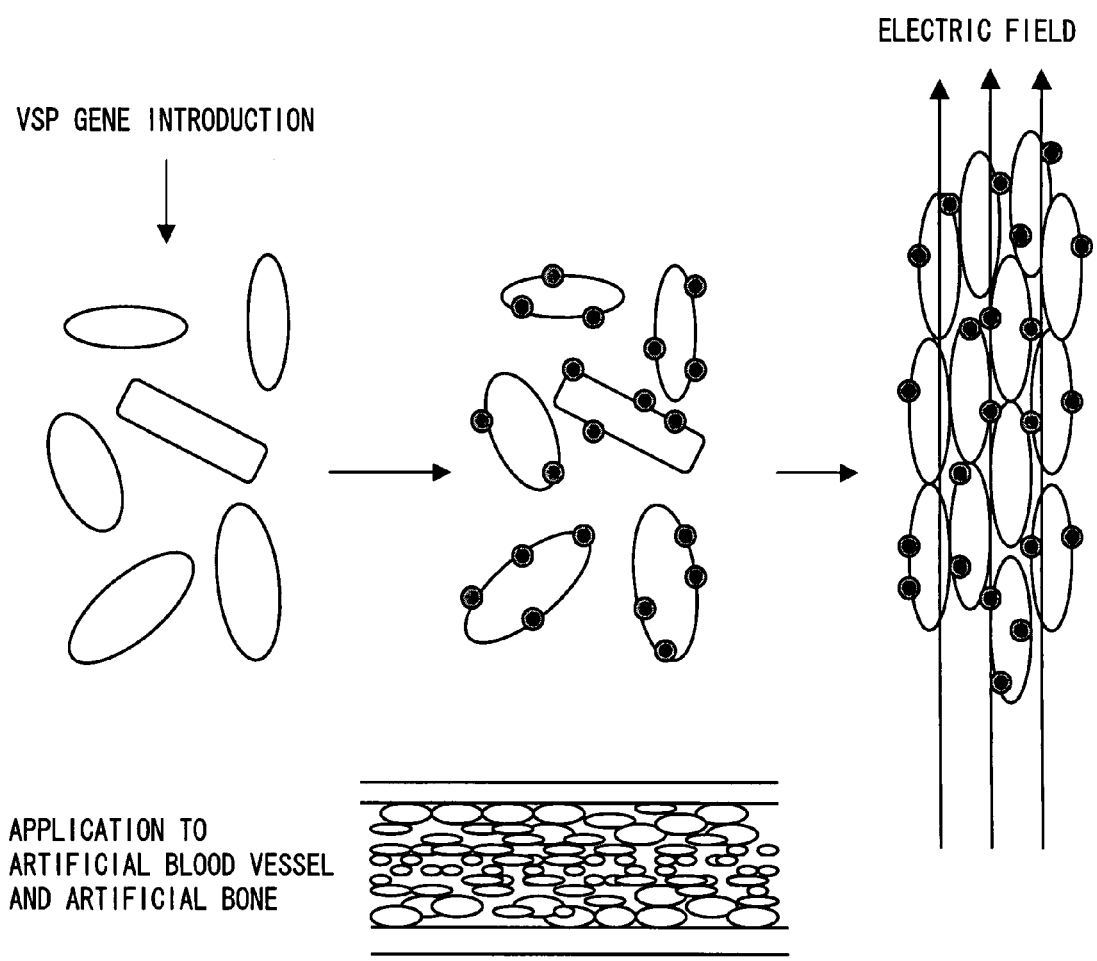
FIG. 9 schematizes an application model based on characteristics of Ci-VSP polypeptide.

By forcing cells to express Ci-VSP by known methods of gene introduction, a local $PIP_3$ concentration in the cell can be controlled membrane-potential dependently. Changes in local intracellular $PIP_3$ concentration are known to control cell form. Therefore, by culturing Ci-VSP expressed cells under certain electric field conditions, a form or arrangement of cells can be controlled electrically. This technique can be used to develop artificial organs of various shapes for use in transplant surgery. FIG. 9 schematizes an application model based on characteristics of Ci-VSP polypeptide.

The following will describe the present invention in more detail by way of examples. It should be appreciated that the invention is not limited in any way by the following examples, and details of the invention may be varied in many ways. Further, the present invention is not limited to the description of the embodiments above, but may be altered by a skilled person within the scope of the claims. An embodiment based on a proper combination of technical means disclosed in different embodiments is encompassed in the technical scope of the present invention.

EXAMPLES

Experimental Procedures

[Preparation of Plasmid]

Reverse transcription PCR was performed using isolated total RNA of adult *Ciona intestinalis* as a template. PCR was run in 30 to 35 cycles consisting of 96° C. for 10 seconds, 60° C. for 5 seconds, and 72° C. for 2 minutes, using primers (5'-CGGGATCCGCCACCATGGAGGGATTC-GACGGTTCAG-3' (SEQ ID NO: 3); 5'-ATAGTT-TAGCGGC CGCCTAAATGTCTTCAGCATCTG-3' (S EQ ID NO: 4)).

The PCR products were inserted into BamHI/NotI sites of pBluescript vector (Stratagene) to subclone Ci-VSP cDNA. Point mutations or deletions were introduced to the cDNA using the QuickChange Site-Directed Mutagenesis available from Stratagene, and the introduction of a mutation was confirmed by determining the sequence.

For expression of Ci-VSP cDNA in *Xenopus* oocyte, pSD64TR and pSD64TF (kindly provided by Dr. T. Snutch) or pGEM HE vector (Promega) were used. cRNA was synthesized with an mMESSAGE mMACHINE kit (Ambion) according to the manufacturer's protocol.

[Electrophysiologic Experiment with *Xenopus* Oocyte]

Oocytes were surgically isolated from an adult female of *Xenopus laevis*, which had first been anaesthetized with 0.15% tricaine solution. GIRK2, or β subunit or γ subunit of G-protein were injected to the oocytes at a concentration ratio of 0.3-0.5 to that of Ci-VSP RNA. IRK1 or IRK1 (R228Q) was injected at a concentration ratio of 0.1 to Ci-VSP RNA.

The oocytes were incubated in ND96 for 2 to 4 days at 17±1° C. Cut-open voltage-clamp recording was performed with CA-1B (DAGAN). Stimulation and data acquisition were performed with a Clampex (Axon Instruments) and Digidata 1322A AD/DA converter. The external solution as a buffer contained 105 mM NMDG-methanesulphonate, 2 mM $CaCl_2$, 10 mM HEPES pH 7.5. The internal solution as a buffer contained 105 mM NMDG-methanesulphonate, 2 mM $MgCl_2$, 0.1 mM EGTA, and 10 mM HEPES (pH 7.5). Internal perfusion was achieved through a glass pipette at 2 μl/minute with a syringe pump.

For measuring Q-OFF currents, two-microelectrode recording was performed with OC-725C available from Warner Instruments. Leakage and symmetrical capacitance currents were subtracted from a holding potential of −80 mV by a P/−10 procedure. In the two-microelectrode recording, the external solution as a buffer contained 96 mM NMDG-Methansulfonate, 3 mM $MgCl_2$, and 5 mM HEPES (pH 7.5).

For expressing Ci-VSP with Kir currents or KCNQ2/3 currents, two-electrode voltage-clamp recording was performed with a 'bath-clamp' amplifier OC-725C. Data acquisition was made with a Macintosh computer, using ITC-16 AD/DA converter and Pulse software (HEKA). The microelectrode resistance ranged from 0.1 to 0.6 megohms. The standard external solution as a buffer contained 92 mM KCl, 3 mM $MgCl_2$, 4 mM KOH, 5 mM HEPES (pH 7.4) for Kir channel recordings.

For measurements of KCNQ2/3 channel currents, a buffer containing 2 mM KCl, 92 mM NaCl, 3 mM $MgCl_2$, 4 mM NaOH, and 5 mM HEPES (pH 7.4) was used.

All of GIRK cRNAs were co-injected with G protein β1 and γ1. Changes in the leakage current of the Kir current were monitored by applying a 100-ms ramp pulse. Data from cells showing a large leakage current at a holding potential of 0 mV or during the ramp pulse were discarded. For measurements of KCNQ2/3, data from cells showing a leakage current equal to or more than 1 mA at a holding potential of −60 mV were discarded.

Output current was filtered by a four-pole Bessel filter at 1 kHz. Sampling frequency was 13-27.7 kHz for two-electrode voltage-clamp recording and 50-100 kHz for cut-open oocytes. All electrical recordings were performed at room temperature in a range of 23±2° C. Data were analyzed with Igor Pro (WaveMetrix Inc.). Statistical significance was determined as P<0.05 with a Mann-Whitney U-test. Results are presented as means ±SD. Error bars in the Figure denote SD.

[In Vitro Assay for Phosphatase Activity]

To express N-terminal fused protein of the cytoplasmic domain of Ci-VSP with the GST gene, the cDNA encoding residues 248-576 of Ci-VSP was subcloned into the EcoRI-XhoI site of pGEX4T3 (Amersham Pharmacia). GST-fused protein was expressed and purified from *E. coli* JM109 with glutathione-sepharose CL-4B (Amersham Pharmacia). Phosphatase activity of Ci-VSP was measured with the methods previously adopted for PTEN phosphatase.

[Immunoblotting and Immunostaining]

Rabbit polyclonal anti-Ci-VSP antibody was raised against a peptide sequence corresponding to amino acid residues 85-96 (ENEHGVDDGRME) SEQ ID NO 16 of Ci-VSP. Sperms of *Ciona intestinalis* were fixed with 0.1 M MOPS (pH 7.0), 0.5 M NaCl, and 4% paraformaldehyde, and permeabilized with Triton X-100. After blocking with 2% goat serum, the sperms were incubated with Ci-VSP antibody (final concentration of 2.5 μg/ml). The antibody was absorbed by the peptide antigen (final concentration of 2.5 μg/ml). As the secondary antibody, a 1:1000 dilution of Alexa 488-conjugated anti-rabbit IgG (Molecular Probes) was used. Specimens were mounted with PermaFluor (Thermo) and observed by a laser-scanning microscope (LSM510; Zeiss). For immunoelectron microscopy, sperms were collected by centrifugation and fixed with 1% glutaraldehyde and 0.23 M phosphate buffer (pH 7.2). Then, sperms were incubated with affinity-purified anti-VSP antibody (60 μg/ml) and with goat anti-rabbit secondary antibody conjugated with 5 nm size gold particle (BioCell, Cardiff). Samples were postfixed with 1% osmium tetraoxide, dehydrated, embedded in Epon812 through propylene oxide, and thin-sectioned with an average thickness of 70 nm.

[Detection of Cell Surface Protein]

Detection of Ci-VSP polypeptide (wildtype or R229Q/R232Q mutant) on cell surface was performed by biotinylation labeling and western blotting. For biotinylation of surface protein, oocytes expressing Ci-VSP polypeptide (wildtype or R229QR232Q mutant) were incubated in 0.5 mg/ml NHS-LC-Biotin (Pierce Biochemical) in ND96 for 8 hours at room temperature. Forty oocytes for each cRNA were homogenized. The resulting supernatant was added to 30 μl of streptavidin beads (Sigma) and collected by centrifugation. The sample was separated by 10% SDS-polyacrylamide gel electrophoresis, followed by western blotting using anti-Ci-VSP polyclonal antibody (0.1 ng/ml) and horseradish peroxidase conjugated anti-rabbit immunoglobulin (Amersham).

Example 2

Ci-VSP Transmembrane Domain functioning as Potential Sensor

The fact that the amino acid sequence of the putative transmembrane domain of Ci-VSP is highly similar to that of the potential sensor of the potential-dependent channel suggests the possibility that the Ci-VSP may be able to detect a change in membrane potential as does the potential-dependent channel. In order to access this, an important experiment was conducted that detected a potential-dependent movement of charge due to a transmembrane shift of the positively charged segment of the potential sensor.

Figure 2:
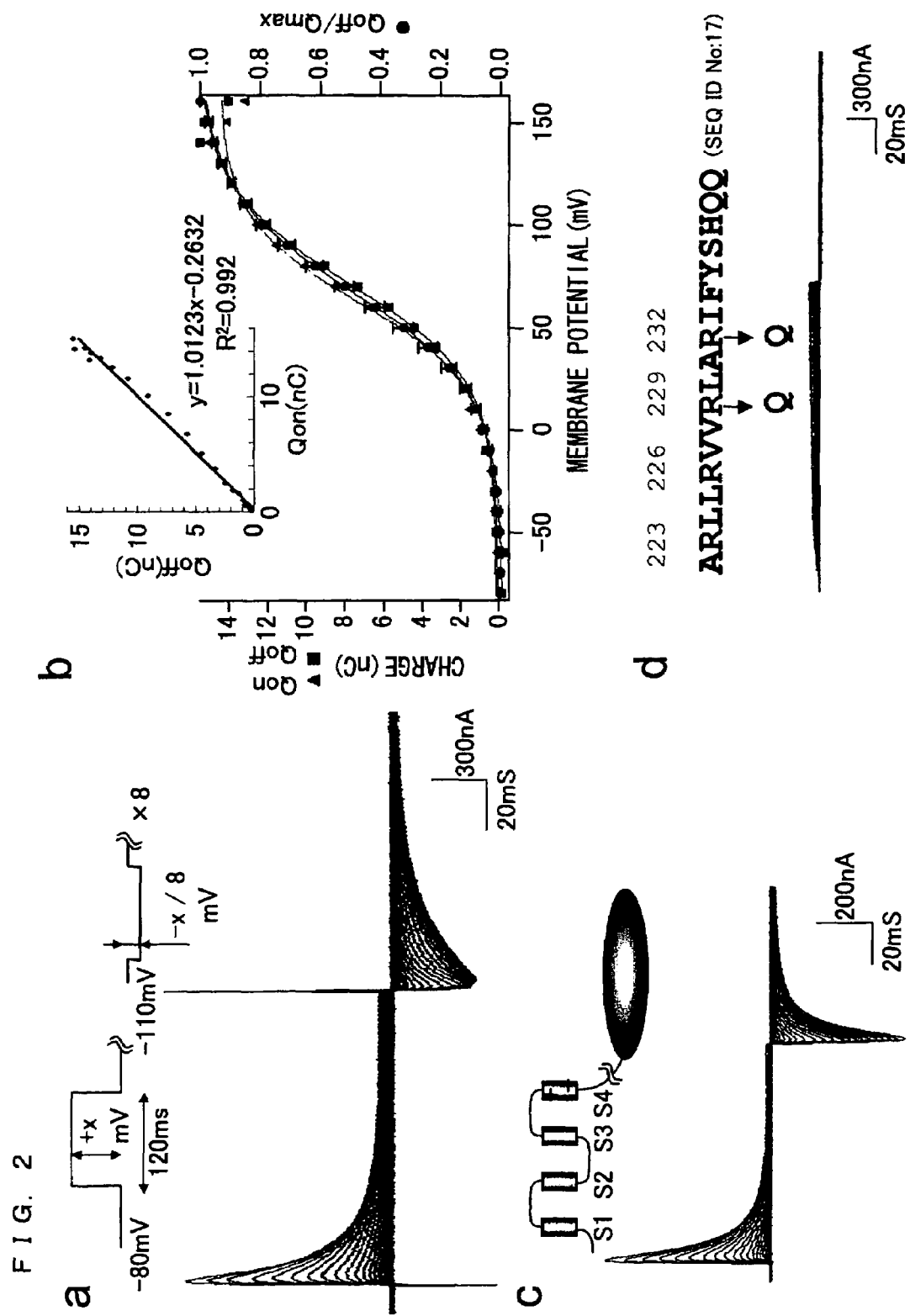
FIG. 2 is a graph showing activity of Ci-VSP transmembrane domain as a potential sensor, in which a is representative example of asymmetrical displacement current from a recording of *Xenopus* cut-open oocyte expressing Ci-VSP; b is a graph comparing carried charges at different membrane potentials, resulting from a change in potential of the gating currents shown in a; c shows displacement currents of the truncated protein lacking the whole carboxy-terminal domain (containing only S1 to S4), as measured by cut-open oocyte recording; and d is a recording from cut-open oocytes expressing Ci-VSP R229Q/R232Q.

FIG. 2a shows a representative example of asymmetrical displacement currents recorded from a cut-open oocyte of *Xenopus laevis* expressing Ci-VSP. A pulse was applied ranging from −80 to +160 mV in 10-mV steps. Linear and symmetrical currents were subtracted from a holding potential of −110 mV by a P/−8 procedure. FIG. 2b is a graph comparing carried charges at different membrane potentials, resulting from a change in potential of the gating currents shown in FIG. 2a; voltage-dependent charges carried by OFF (solid squares) current and ON (solid triangles) current from a cut-open oocyte; and OFF (solid circles) current recorded under TEVC (n=10). The ON and OFF-current trace was fitted by single exponential $(I(t)=Ae-t/\tau+C)$, where A is the peak current amplitude. The carried charge was calculated by integrating each current for a duration of $3\tau$ starting from the initiation point of the pulse. Q-OFF from TEVC recording was measured by integrating each OFF 'gating' current for 150 ms from the start point of the repolarization. The Q-V curve was fitted by a Boltzmann relation, $Q=1/[1+\exp\{Ze(V-V1/2)/kT\}]$, where k is the Bolzmann constant and e the elementary electric charge). In cut-open oocytes, V1/2 values were 62.7 and 71.8 mV, and Z values were 1.26 and 1.098 for Qon and Qoff, respectively. Qoff from TEVC recording (n=10) was fitted with 68.5 mV for V1/2 and 1.03 for Z. Maximum charge movement of OFF-current under TEVC was 40.2±14.2 nC (n=10). The inset shows an X-Y plot of Qoff and Qon from the same cut-open oocyte as shown in FIG. 2a.

cRNAs of Ci-VSP were microinjected into *Xenopus* oocytes and asymmetric displacement currents were recorded with two-electrode voltage-clamp (TEVC) and cut-open oocytes. Oocytes expressing Ci-VSP showed robust transient outward currents in response to depolarization and inward currents in response to hyperpolarization, resembling the ON and OFF gating currents of voltage-gated channels, respectively (FIG. 2a). One of the distinct characteristics of the "gate" current is that movement of charge occurs voltage dependently. A Q-V curve of the ON current was fitted with the Boltzmann equation with 62.7 mV for V1/2 and 1.26 for Z. This resembled that of the OFF current (V1/2=71.7 mV, Z=1.1) (FIG. 2b). The carried charge of the ON current coincides with that of the OFF current over a wide range of membrane voltages, as clearly indicated by the X-Y plot of the integrated total charge for the ON current against the integrated total charge for the OFF current (FIG. 2b, inset). Thus, the same molecular structure, which is a cause of charge movement in depolarization, forms the basis of charge movement in repolarization. Compared with the voltage-dependent channel such as the Shaker-type K+ channel, the voltage dependence of charge movement was significantly shifted positively (V1/2 of +60 mV for Ci-VSP, compared with −37.9 mV for the Shaker K+ channel) and the slope (stepness) was less steep (Z=1.8 in the ON current of the Shaker K+ channel, compared with Z=1.1 in the ON current of Ci-VSP).

In order to confirm that such a channel-like "gating" current results from the transmembrane segment, a truncated protein at residue 256 (lacking the whole carboxy-terminal enzyme domain) was expressed. FIG. 2c represents displacement currents of the truncated protein lacking the whole carboxy-terminal domain (containing only S1 to S4), as measured by cut-open oocyte recording. It was found as a result that the truncated protein containing only S1 to S4 had the properties as a potential sensor as does the full-length protein. However, the Q-V curve slightly shifted to the right (not shown).

It is known that the positive charges in the S4 segment form the basis of charge movement in the potential sensor and are indispensable for the gating of the potential-dependent channel. In order to access whether the positive charges in the S4-like segment are necessary for the "gating" current of C-VSP as in the potential-dependent channel, some of the positively charged residues in the S4-like segment were mutated.

The "gating" current disappeared completely when two alanines (R223 and R226) among the four positively charged residues were mutated to the neutral glutamine (FIG. 2d). FIG. 2d depicts a recording from cut-open oocytes expressing Ci-VSP R229Q/R232Q. It was found that the properties of Ci-VSP as a potential sensor were dependent on charge of the basic amino acids in S4.

In order to check whether the introduction of two mutations has inhibited expression in the cell surface, the protein on the cell surface was biotinylated and specific detection was made by western blotting using anti-Ci-VSP antibody. As a result, clear signals were detected from R229Q/R232Q protein. This suggests the possibility that the absence of gating current in the R229Q/R232Q mutant is not due to failure to target this mutant protein.

As described above, strong voltage-dependent gating current was detected from Ci-VSP. The ON current did not saturate above 100 mV. In the voltage-clamp technique, the presence of intrinsic ion current made it difficult to accurately access G-V relationship. This was overcome by the cut-open oocyte voltage-clamp technique involving internal perfusion. According to this technique, the G-V curve of the ON current substantially coincided with that of the OFF current. This suggests that the Ci-VSP is free of voltage-dependence of gating current.

The truncated protein lacking the carboxyl-terminal enzyme domain showed gating current but the voltage dependence shifted to the right. The gating current disappeared completely when two of the four positively charged amino acid residues in the S4-like segment were mutated to neutral amino acids. These results suggest that the Ci-VSP has the activity of a potential sensor as does the voltage-gated channel.

Example 3

Cytoplasmic Domain of Ci-VSP as Phosphoinositide Phosphatase

According to the procedure described in Example 1, assessment was made to show that the cytoplasmic domain of Ci-VSP polypeptide is phosphoinositide phosphatase (FIG. 3). FIG. 3a is a diagram comparing amino acid sequence of the phosphatase active center of Ci-VSP with that of PTEN in various species. The Ci-VSP polypeptide has the active center similar to that of known phosphatase.

As shown in FIG. 3a, the phosphatase-like domain of Ci-VSP is highly homologous to PTEN. PTEN has phosphatidylinositol which is dephosphorylated at the 3-site of its inositol ring.

To see whether the Ci-VSP has phosphatase activity that uses $PI(3, 4, 5)P_3$ as a substrate, a fusion protein of GST and the whole C-terminal cytoplasmic region of Ci-VSP was synthesized. FIG. 3b represents phosphoinositide phosphatase activity of the fusion protein of glutathione s-transferase and the phosphatase-like domain of Ci-VSP by a malachite green assay using $PI(3, 4, 5)P_3$ as a substrate. Reaction with the GST-fused Ci-VSP cytoplasmic domain (GST-Ci-VSPΔTM, 2 µg/tube) (solid square) was performed at 23° C., and the reaction was terminated at indicated time. Measurement of released inorganic phosphate was performed by comparison with standard inorganic phosphate. As negative controls, inactive mutant GST-Ci-VSPΔTM(C363S) (solid circle) and GST (solid triangle) were used. BIOMOL GREEN™ reagent (Biomol, Plymouth Meeting, Pa.) was added to the sample and $OD_{600}$ was measured by using $H_2O$ as a reference. Each data was assayed in duplicate and averaged. As shown in FIG. 3b, the cytoplasmic domain of Ci-VSP showed phosphoinositide phosphatase activity. The enzyme activity was found to be time-dependent. Experiment was repeated twice, which had the same result.

It was therefore found that the substrate of enzyme activity in the enzyme domain of Ci-VSP polypeptide was the phospholipid $PIP_3$, which is a substance that plays important roles in intracellular signal transmission in, for example, canceration, morphological alteration, or cell death. In expression of Ci-VSP polypeptide as GST-fused protein in *E. coli*, measurement of $PIP_3$ phosphatase activity found that dephosphorylation of $PIP_3$ to $PIP_2$ had occurred.

Example 4

Enzyme Activity of Ci-VSP

Enzyme activity of Ci-VSP was examined with thin layer chromatography (TLC). The fusion protein (GST-Ci-VSP) of GST and the whole carboxyl-terminal cytoplasmic region of Ci-VSP described in Example 3 was incubated with a fluorescent-labeled substrate (NBD6-$diC_6$-PI $(3, 4, 5)P_3$). Where there is enzyme activity using $PI(3, 4, 5)P_3$ as a substrate, the degraded product $PIP_2$(NBD6-$diC_6$-PI$(4, 5)P_2$) is detected.

Figure 4:
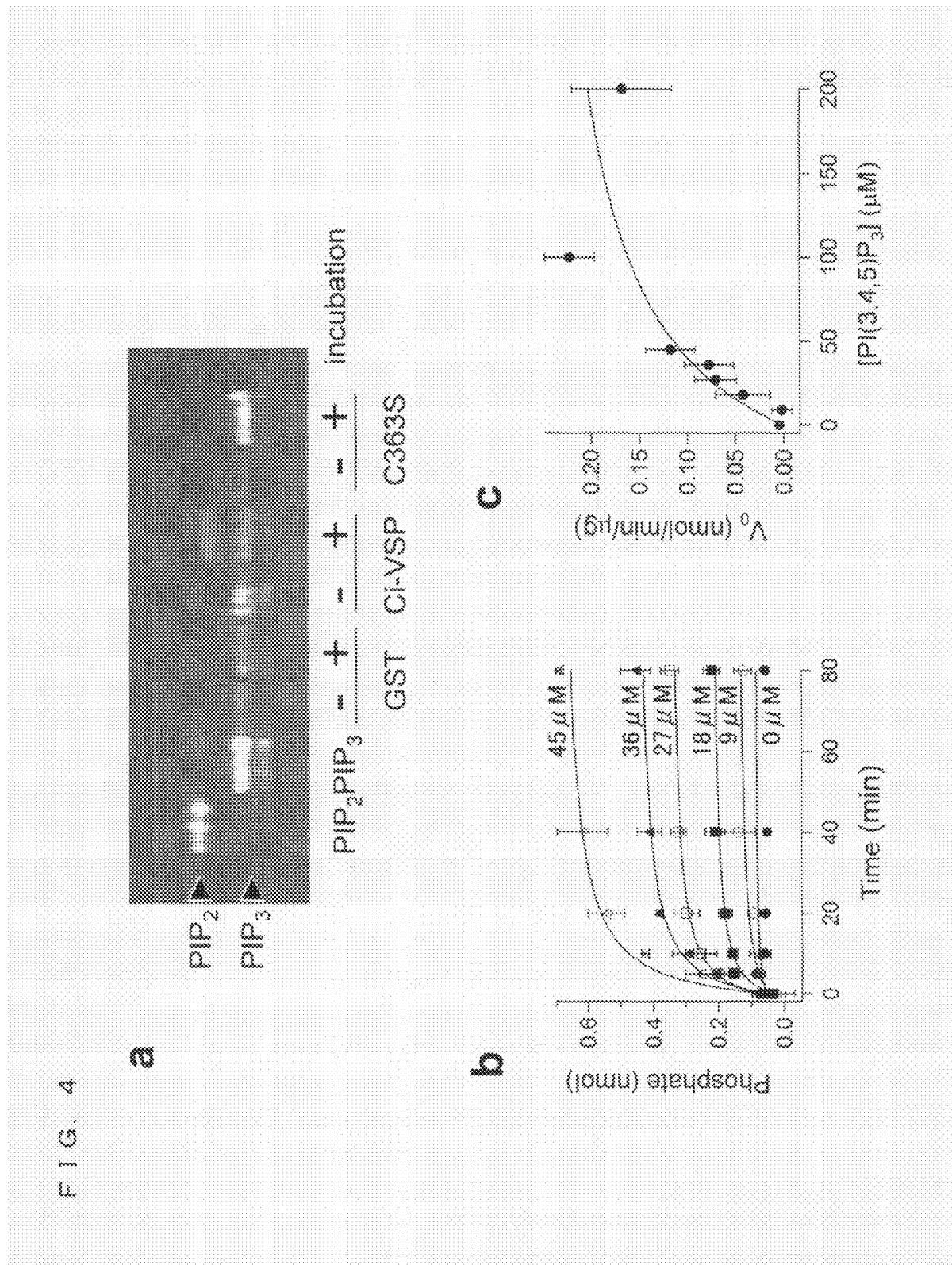
FIG. 4 shows results of examination on Ci-VSP enzyme activity, in which a represents the result of Ci-VSP enzyme activity by thin layer chromatography (TLC); and b and c represent the rate of enzyme activity calculated by Malachite green assay.

As shown in FIG. 4a, Ci-VSP was found to have desired activity; however, no $PIP_2$ band could be detected in the protein (C363S) that had a serine-for-cysteine substitution in the active center, or when GST was incubated with the substrate (FIG. 4a).

Concerning the cytoplasmic domain of Ci-VSP, a further study was made as to characteristics of enzyme activity using phosphoinositide as a substrate. Specifically, enzyme reaction using various concentrations of substrate $PIP_3$ was performed with a malachite green assay to access time-dependence of the reaction.

Malachite green imparts pale yellow in the absence of inorganic phosphate. In the presence of inorganic phosphate with ammonium molybdate, malachite green shows concentration-dependent changes to dark green. Thus, by measuring absorbance of malachite green at 620 nm, the inorganic phosphate that is generated by the degradation of $PI(3, 4, 5)P_3$ to $PI(4, 5)P_2$ can be quantified. Measurement of Ci-VSP enzyme activity at varying substrate concentrations in the presence of malachite green confirmed a time-dependent release of inorganic phosphate, as shown in FIG. 4b.

In the graph of FIG. 4b, slopes at t=0 (minute) were calculated to determine initial rate $V_0$ of enzyme reaction for each substrate concentration, and the results were plotted against substrate concentration (FIG. 4c). The curve was fitted with the Michaelis-Menten relation, and the maximum rate Vmax and the substrate concentration Km required for 1/2 Vmax were obtained. Vmax was 0.292 nmol/min/µg, and Km was 36 µM. These values are close to values reported in PTEN, suggesting that the enzyme activity of the region in the cytoplasmic domain of Ci-VSP is indeed similar to that of PTEN.

Example 5

Potential-Dependent Change of Phosphoinositide Dynamics by Ci-VSP

The results of Examples 2 and 3 indicate that the Ci-VSP functions as not only as a potential sensor but as phosphoinositide phosphatase as well. In order to examine whether the enzyme activity of Ci-VSP could be modified by membrane potential, assessment was made as to whether the dephosphorylation activity ($PIP_3$ to $PIP_2$) of the Ci-VSP polypeptide is changed by membrane potential, according to the procedure described in Example 1.

Figure 5:
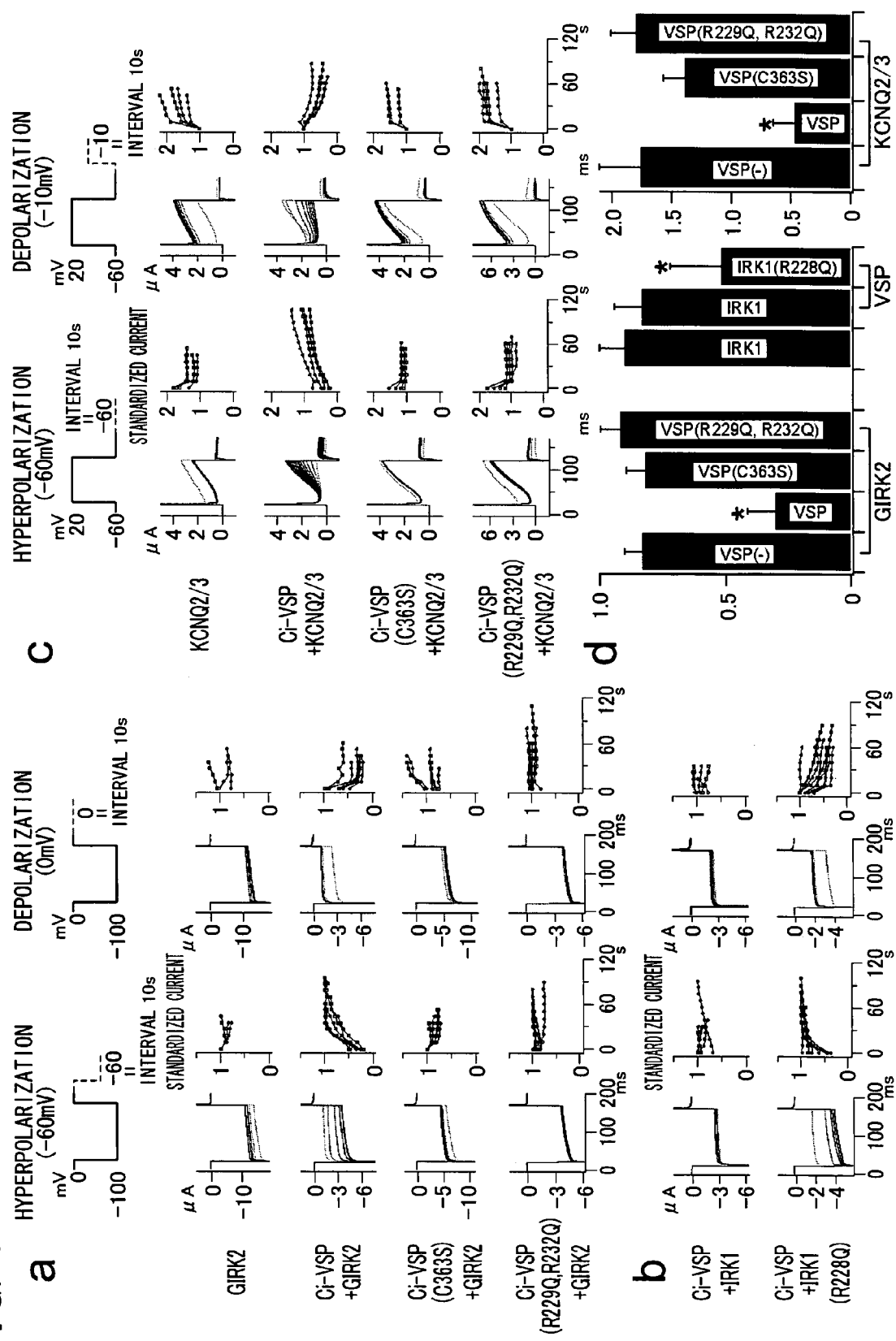
FIG. 5 shows potential-dependent changes in phosphoinositide dynamics by Ci-VSP as probed with $K^+$ channel activities, in which a show graphs plotting traces of transient changes of GIRK currents and current amplitudes; b shows graphs plotting changes in IRK1 current traces and current amplitudes against time on expression with Ci-VSP; c shows graphs plotting changes in KCNQ2/3 current traces and current amplitudes over time in oocytes expressing wildtype Ci-VSP, C363S mutant, or R229Q/R232Q mutant; and d shows graphs summarizing potential-dependent changes of potassium channel quantity.

Specifically, the GIRK2, IRK1, or KCNQ2/3 potassium channel ($PIP_2$ susceptible protein) was expressed with bovine G protein β1 and γ1 in the presence or absence of Ci-VSP. By recording Kir current using TEVC method, potential-dependent changes of phosphoinositide dynamics by Ci-VSP were observed using $K^+$ channel activity as a probe (FIG. 5).

FIG. 5a shows graphs plotting traces of transient changes of GIRK currents and current amplitudes. The four representative traces are from cells expressing GIRK2 only, GIRK2+Ci-VSP, GIRK2+Ci-VSP mutant (C363S), or GIRK+Ci-VSP mutant (R229Q/R232Q). The GIRK currents were activated at −100 mV for 150 ms, and with 10-s intervals at either −60 mV (left) or 0 mV (right). The thickness of the traces indicates the order of recording with a series of test pulses. Thicker traces were recorded later. As shown in FIG. 5a, GIRK2 currents changed according to changes in membrane potential only when GIRK2 is expressed with wildtype VSP (increase on hyperpolarization, decrease on depolarization).

FIG. 5b shows graphs plotting changes in IRK1 current traces and current amplitudes against time on expression with Ci-VSP. In the continuous time plots of FIGS. 5a and 5b, the amplitude of Kir current during each test pulse was standardized by the maximum amplitude obtained in the series of recordings that were made with the voltages of intervals between test pulses held at −60 mV. As shown in FIG. 5b, similar changes were observed in the IRK1 mutant that had altered concentration-dependence of $PIP_2$ susceptibility.

FIG. 5c shows graphs plotting changes in KCNQ2/3 current traces and current amplitudes over time in oocytes expressing wildtype Ci-VSP, C363S mutant, or R229Q/R232Q mutant. In the continuous time plots, the peak amplitude of outward current during 100-ms depolarization at +20 mV was standardized by the peak amplitude of outward current during the first test pulse of the series using an interval potential at −10 mV. As shown in FIG. 5c, the activity increased on hyperpolarization and decreased on depolarization in the KCNQ2/3 channel showing M current.

FIG. 5d shows graphs summarizing potential-dependent changes of potassium channel quantity. The bars on Kir channel (left) indicate mean values of minimum inward currents on stimulation at −100 mV, with respect to the maximum amplitude in the recordings from the same cell. The bars on KCNQ2/3 (right) indicate amplitudes of outward currents in the series of experiments that were performed with the voltages of intervals between test pulses held at −10 mV, as standardized by the amplitude of the outward current induced by the first test pulse. Asterisk indicates a statistically significant difference from Ci-VSP(−) cells in each set.

As described above, the level of channel activity showed a quantitative change according to changes in membrane potential, when the GIRK channel or KCNQ2/3 channel, which are known to activate Ci-VSP polypeptide with $PIP_2$, was expressed with VSP. That is, the enzyme activity increased and decreased by the hyperpolarization and depolarization, respectively, of membrane potential.

Example 6

Potential-Dependence of Phosphatase Activity

Potential-dependence of phosphatase activity as probed with $K^+$ channel activities was examined (FIG. 6). FIG. 6a shows graphs of representative recordings of GIRK currents from oocytes expressing Ci-VSP and GIRK2, using membrane potential levels with varied voltages during intervals between test pulses ranging from −80 mV to 20 mV. Intervals were set to 60s, because the current amplitudes reached a certain level within this time period in almost all recordings in FIG. 5.

FIG. 6b is a plot of current amplitudes of GIRK currents against membrane potential levels during intervals between test pulses. Records from four different cells are shown as distinct symbols. Inward currents at the end of a test pulse causing hyperpolarization at −100 mV were plotted against voltages of intervals between test pulses. The curves were fitted with the relation: $I=1/[1+\exp(V1/2-V)k]]+C$, where V1/2 is the voltage required to suppress half of the activity, k is the slope of potential-dependence, and C is the sustainable factor of current. Dotted line is the standardized Q-V curve of potential sensor movement, similar to that shown in FIG. 2.

Example 7

Roles of Linker Region

Roles of the linker region flanking the potential sensor domain and phosphatase domain of the Ci-VSP polypeptide were examined.

Figure 7:
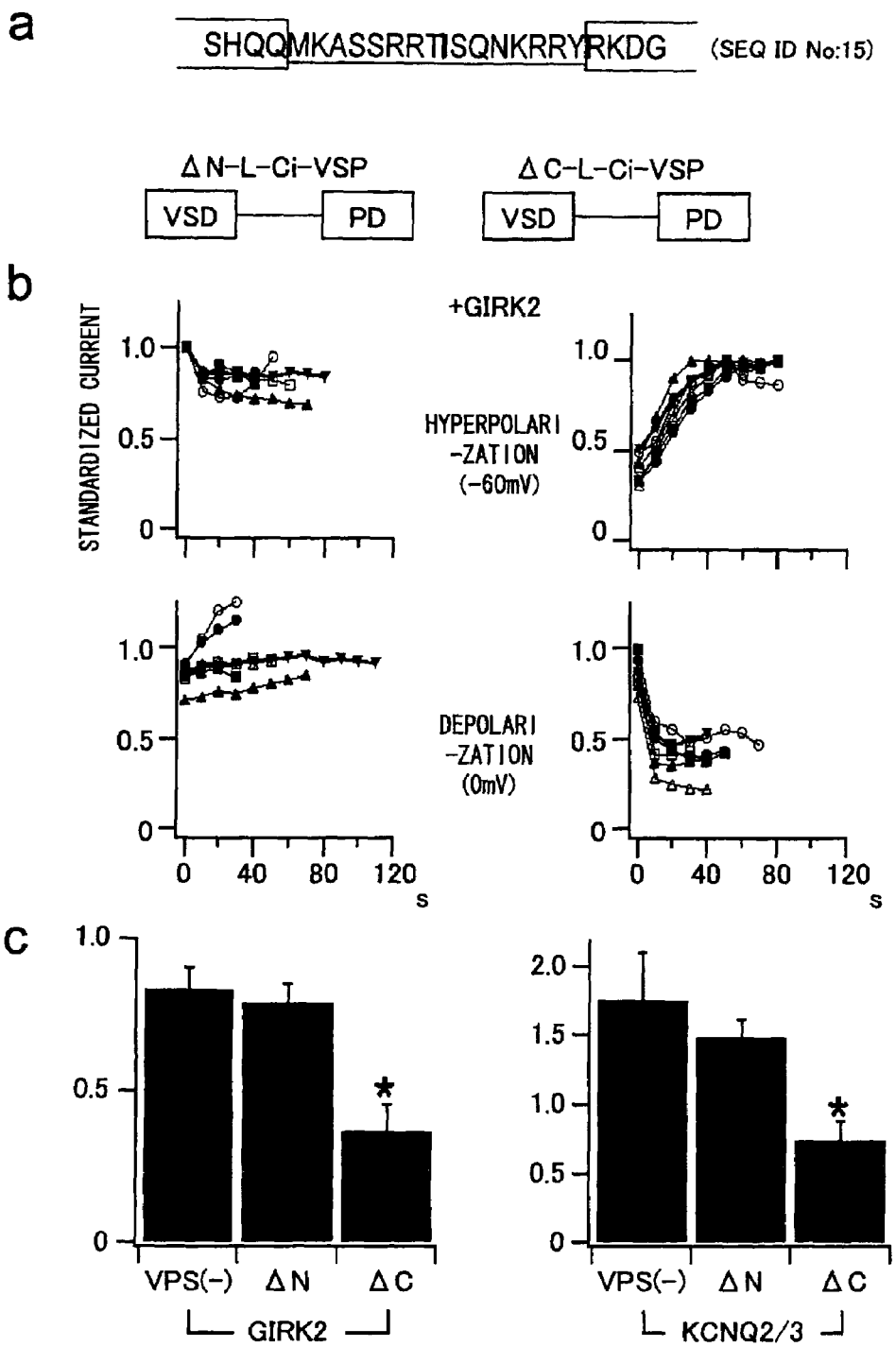
FIG. 7 is a diagram representing that the linker region flanking the potential sensor domain and phosphatase domain is important for the coupling, in which a shows the linker region (MKASSRRTISQNKRRY) SEQ ID NO: 15 flanking the S4-like segment and phosphatase-like domain; b shows graphs representing transient changes of Kir currents on hyperpolarization or depolarization during intervals of test pulses; and c shows graphs summarizing data concerning expression with GIRK2 (left) or KCNQ2/3 (right), in interval series at varying membrane potentials.

FIG. 7a shows the linker region (MKASSRR-TISQNKRRY: SEQ ID NO: 5) flanking the S4-like segment and phosphatase-like domain. N-terminal or C-terminal half of the linker region was deleted (ΔN-L-Ci-VSP and ΔC-L-Ci-VSP, respectively), and the linker region was expressed in oocytes together with GIRK2 or KCNQ2/3. VSD and PD denote sensor domain and phosphatase domain, respectively.

FIG. 7b shows graphs representing transient changes of Kir currents on hyperpolarization or depolarization during intervals of test pulses.

FIG. 7c shows graphs summarizing data concerning expression with GIRK2 (left) or KCNQ2/3 (right), in interval series at varying membrane potentials. Current amplitudes were standardized as in FIG. 5d. Asterisk indicates that the cells with ΔN-L-Ci-VSP have no significant difference in current amplitude from cells expressing no Ci-VSP, i.e., no coupling between potential sensor and phosphatase.

It was found from FIG. 7a to FIG. 7c that (1) the Ci-VSP polypeptide had both the potential sensor module and the enzyme module, and that these modules were linked together by a short linker sequence, and (2) enzyme activity was regulated potential dependently by the coupling of the two domains that exist in a single molecule of Ci-VSP polypeptide. That is, the linker sequence was found to be necessary for the regulation of enzyme activity of the enzyme module (phosphatase domain) based on electrical signals detected by the potential sensor module.

Example 8

Localization of Ci-VSP

To find the physiological role of Ci-VSP, gene expression patterns of Ci-VSP were examined. RT-PCR of Ci-VSP transcripts in heart, somatic muscle, genital gland, and testis revealed testis-specific expression of Ci-VSP polypeptide (FIG. 8a).

Immunohistochemistry was performed on *Ciona intestinals* sperm with a polyclonal antibody against the C-terminal peptide sequence of Ci-VSP (FIGS. 8b to 8g).

FIGS. 8b to 8d show fluorescence observed in the flagella of sperms, and mitochondria. FIGS. 8e to 8g show results in which the antibody preabsorbed with antigenic peptide was used as the primary antibody. Scale bar is 10 μm. FIGS. 8h to 8k represent immunoelectron localization of Ci-VSP at plasma membrane of sperm flagella. Cross sections (h, i) and longitudinal sections (j, k) of the flagella are shown.

The peripheral regions of the flagellar axonemes were labeled as shown in the Figures. The same patterns were also observed with a different antibody (antibody against N-terminal peptide) (not shown). Debris of plasma membrane are associated (arrows).

Gold particles were found only on the debris of partly disrupted plasma membrane (arrows), but not on apparently intact plasma membrane (arrowhead in i). This reflects the accessibility of the antibody, which was raised against the N-terminal intracellular domain of Ci-VSP. Scale bar is 200 nm (the scale bar in i also applies to h to j).

This revealed that the Ci-VSP polypeptide was localized in sperm tail.

The embodiments and concrete examples of implementation discussed in the foregoing detailed explanation serve solely to illustrate the technical details of the present invention, which should not be narrowly interpreted within the limits of such embodiments and concrete examples, but rather may be applied in many variations within the spirit of the present invention, provided such variations do not exceed the scope of the patent claims set forth below.

INDUSTRIAL APPLICABILITY

By revealing the conjugate principle of the phosphatase domain and potential sensor of a polypeptide according to the present invention, the invention can be used as a tool for electrically controlling enzyme activity. Such a tool is usable in the basic technology of nano-biotechnology. With a polypeptide according to the present invention as a novel potential sensor molecule, an interface between electrical signal and chemical signal can be established. This contributes to development of medical engineering linking biological signals to electrical circuits. That is, a polypeptide according to the present invention is highly useful as a biological material for developing interface bio-elements.

The invention claimed is:

1. An isolated polypeptide capable of functioning as a voltage sensor, consisting of
   amino acids 1-239 of SEQ ID NO:2.

2. An isolated polypeptide capable of functioning as a voltage sensor, encoded by:
   (a) a polynucleotide consisting of nucleotides 1-717 of SEQ ID NO: 1;
   (b) a polynucleotide that hybridizes with a polynucleotide complementary to nucleotides 1-717 of SEQ ID NO: 1 under hybridization conditions of 5× SSC at 42° C., and wash conditions of 0.1× SSC at about 65° C.; or
   (c) a polynucleotide at least 99% identical to the nucleotides 1-717 of SEQ ID NO:1.

3. An isolated polypeptide capable of functioning as a voltage sensor, consisting of
   amino acids 1-255 of SEQ ID NO:2.

4. An isolated polypeptide capable of functioning as a voltage sensor, encoded by:
   (a) a polynucleotide consisting of nucleotides 1-765 of SEQ ID NO:1;
   (b) a polynucleotide that hybridizes with a polynucleotide complementary to nucleotides 1-765 of SEQ ID NO: 1 under hybridization conditions of 5× SSC at 42° C., and wash conditions of 0.1× SSC at about 65° C.; or
   (c) a polynucleotide at least 99% identical to nucleotides 1-765 of SEQ ID NO: 1.

5. An isolated polypeptide which consists of the amino acid sequence of SEQ ID NO:5.

6. An isolated polypeptide capable of converting electrical signals to chemical signals without need of direct ion flow, said polypeptide consisting of
   the amino acid sequence of SEQ ID NO:2.

7. An isolated polypeptide capable of converting electrical signals into chemical signals without need of direct ion flow, said polypeptide encoded by:
   (a) a polynucleotide consisting of the nucleotide sequence of SEQ ID NO:1;
   (b) a polynucleotide that hybridizes with a polynucleotide complementary to the nucleotides of SEQ ID NO: 1 under hybridization conditions of 5× SSC at 42° C., and wash conditions of 0.1× SSC at about 65° C.; or
   (c) a polynucleotide at least 99% identical to the nucleotide sequence of SEQ ID NO: 1.

8. An isolated polypeptide consisting of amino acids 85-96 of SEQ ID NO:2.

9. An isolated polypeptide having a phosphoinositide phosphatase activity, consisting of
   amino acids 256-576 of SEQ ID NO:2.

10. An isolated polypeptide having a phosphoinositide phosphatase activity, encoded by:
    (a) a polynucleotide consisting of nucleotides 766-1728 of SEQ ID NO: 1;
    (b) a polynucleotide that hybridizes with a polynucleotide complementary to the nucleotides 766-1728 of SEQ ID NO: 1 under hybridization conditions of 5× SSC at 42° C., and wash conditions of 0.1× SSC at about 65° C.; or
    (c) a polynucleotide at least 99% identical to the nucleotides 766-1728 of SEQ ID NO:1.

* * * * *

SEQUENCE LISTING

```
<160> NUMBER OF SEQ ID NOS: 5

<210> SEQ ID NO 1
<211> LENGTH: 1029
<212> TYPE: DNA
<213> ORGANISM: Ciona intestinals

<400> SEQUENCE: 1
atggaaggcg ataattgcaa taaatctcgt cataaaagcc acaacatgat taaccctaat    60
tatgcaagtg tacgatgtac acaacctctt ccatctgtaa tccaacttcg atctcgaaac   120
aaaatgattg gcatcactga agacccttct tcagactctg aacccgtatc ctccaaccag   180
ccattattgc tcacaaattt aagttacgag gtgcatacat ttaacgacaa caataatcat   240
gagcgtcccg caccccaaga acaatctaca caaaacacta tgatttcaat gcaatcagaa   300
caaaaatcag atcgattcac cgcttccaac cttgggatgt tccaatacat gaagtttgag   360
ataggagaag atggagatga tcatgaggaa gaagcaatcc tcacgaacag ggagaaactg   420
agacacatcc ttcattctaa accaatacat gttgcaatca tagtcctagt agtgttggac   480
agtttccttg tagttggtga actccttatt gacctcaaag taatcattgt accacatggt   540
aatcccgcac cagagatatt acacgggttt tctctctcaa ttctatcaat atttatggtg   600
gaaatcgctt tgaagataat cgccgatcat cgtcacttca tacaccacaa ggtggaagtg   660
ttggatgcgg ttgtcgtggt gatatcgttc ggtgtcgata tcgctcttat attcgtcggg   720
gagagtgaag ccctcgctgc tatcggactc cttgtcattc tacggctgtg gagagtcttc   780
```

-continued

```
agaatcatta atggtatcat cgtaacagta aaaactaaag cagacgatag agttcatgaa    840
ataaagaaaa agaattctga gctggaatta caaattcata atctagaaga gaaactctca    900
caaaaggagc aagatatgtc ccgcctgcat gagattctac gttgcaataa tatcgatatc    960
ccaccaacag tgcctttaac tacttcagtg caaatccata gtaccacaac agcctctgct   1020
gatgtttaa                                                           1029
```

<210> SEQ ID NO 2
<211> LENGTH: 576
<212> TYPE: PRT
<213> ORGANISM: Ciona intestinals

<400> SEQUENCE: 2

```
Met Glu Gly Phe Asp Gly Ser Asp Phe Ser Pro Pro Ala Asp Leu Val
1               5                   10                  15

Gly Val Asp Gly Ala Val Met Arg Asn Val Asp Val Thr Ile Asn
                20                  25                  30

Gly Asp Val Thr Ala Pro Pro Lys Ala Ala Pro Arg Lys Ser Glu Ser
            35                  40                  45

Val Lys Lys Val His Trp Asn Asp Val Asp Gln Gly Pro Ser Glu Lys
 50                  55                  60

Pro Glu Thr Arg Gln Glu Arg Ile Asp Ile Pro Glu Ile Ser Gly
 65                  70                  75                  80

Leu Trp Trp Gly Glu Asn Glu His Gly Val Asp Asp Gly Arg Met Glu
                85                  90                  95

Ile Pro Thr Thr Gly Val Gly Arg Val Gln Phe Arg Val Arg Ala Val
                100                 105                 110

Ile Asp His Leu Gly Met Arg Val Phe Gly Val Phe Leu Ile Phe Leu
            115                 120                 125

Asp Ile Ile Leu Met Ile Ile Asp Leu Ser Leu Pro Gly Lys Ser Glu
130                 135                 140

Ser Ser Gln Ser Phe Tyr Asp Gly Met Ala Leu Ala Leu Ser Cys Tyr
145                 150                 155                 160

Phe Met Leu Asp Leu Gly Leu Arg Ile Phe Ala Tyr Gly Pro Lys Asn
                165                 170                 175

Phe Phe Thr Asn Pro Trp Glu Val Ala Asp Gly Leu Ile Ile Val Val
            180                 185                 190

Thr Phe Val Val Thr Ile Phe Tyr Thr Val Leu Asp Glu Tyr Val Gln
            195                 200                 205

Glu Thr Gly Ala Asp Gly Leu Gly Arg Leu Val Val Leu Ala Arg Leu
        210                 215                 220

Leu Arg Val Val Arg Leu Ala Arg Ile Phe Tyr Ser His Gln Gln Met
225                 230                 235                 240

Lys Ala Ser Ser Arg Arg Thr Ile Ser Gln Asn Lys Arg Arg Tyr Arg
                245                 250                 255

Lys Asp Gly Phe Asp Leu Asp Leu Thr Tyr Val Thr Asp His Val Ile
            260                 265                 270

Ala Met Ser Phe Pro Ser Ser Gly Arg Gln Ser Leu Phe Arg Asn Pro
        275                 280                 285

Ile Gly Glu Val Ser Arg Phe Phe Lys Thr Lys His Pro Asp Lys Phe
    290                 295                 300

Arg Ile Tyr Asn Leu Cys Ser Glu Arg Gly Tyr Asp Glu Thr Lys Phe
305                 310                 315                 320

Asp Asn His Val Tyr Arg Val Met Ile Asp Asp His Asn Val Pro Thr
```

-continued

```
                325                 330                 335
Leu Val Asp Leu Leu Lys Phe Ile Asp Asp Ala Lys Val Trp Met Thr
            340                 345                 350
Ser Asp Pro Asp His Val Ile Ala Ile His Cys Lys Gly Gly Lys Gly
            355                 360                 365
Arg Thr Gly Thr Leu Val Ser Ser Trp Leu Leu Glu Asp Gly Lys Phe
            370                 375                 380
Asp Thr Ala Lys Glu Ala Leu Glu Tyr Phe Gly Ser Arg Arg Thr Asp
385                 390                 395                 400
Phe Glu Val Gly Asp Val Phe Gln Gly Val Glu Thr Ala Ser Gln Ile
                405                 410                 415
Arg Tyr Val Gly Tyr Phe Glu Lys Ile Lys Lys Asn Tyr Gly Gly Gln
            420                 425                 430
Leu Pro Pro Met Lys Lys Leu Lys Val Thr Gly Val Thr Ile Thr Ala
            435                 440                 445
Ile Gln Gly Val Gly Arg Gly Asn Gly Ser Asp Leu Ser Met Gln Ile
        450                 455                 460
Val Ser Glu Arg Gln Glu Val Leu Leu Cys Lys Phe Ala Glu Gly Tyr
465                 470                 475                 480
Asn Cys Ala Leu Gln Tyr Asp Ala Thr Asp Cys Val Thr Cys Glu
            485                 490                 495
Val Lys Asn Cys Pro Val Leu Ala Gly Asp Ile Lys Val Arg Phe Met
                500                 505                 510
Ser Thr Ser Lys Ser Leu Pro Arg Gly Tyr Asp Asn Cys Pro Phe Tyr
            515                 520                 525
Phe Trp Phe Asn Thr Ser Leu Val Glu Gly Asp His Val Thr Leu Lys
            530                 535                 540
Arg Glu Glu Ile Asp Asn Pro His Lys Lys Thr Trp Lys Ile Tyr
545                 550                 555                 560
Arg Asp Asn Phe Thr Val Lys Leu Thr Phe Ser Asp Ala Glu Asp Ile
                565                 570                 575

<210> SEQ ID NO 3
<211> LENGTH: 36
<212> TYPE: DNA
<213> ORGANISM: Artificial Sequence
<220> FEATURE:
<223> OTHER INFORMATION: Description of Artificial Sequence:
      primer for amplifying CiVSP gene

<400> SEQUENCE: 3
cgggatccgc caccatggag ggattcgacg gttcag                         36

<210> SEQ ID NO 4
<211> LENGTH: 36
<212> TYPE: DNA
<213> ORGANISM: Artificial Sequence
<220> FEATURE:
<223> OTHER INFORMATION: Description of Artificial Sequence:
      primer for amplifying CiVSP gene

<400> SEQUENCE: 4
atagtttagc ggccgcctaa atgtcttcag catctg                         36

<210> SEQ ID NO 5
<211> LENGTH: 16
<212> TYPE: PRT
<213> ORGANISM: Ciona intestinals
```

```
<400> SEQUENCE: 5

Met Lys Ala Ser Ser Arg Arg Thr Ile Ser Gln Asn Lys Arg Arg Tyr
1               5                   10                  15
```